(12) United States Patent　　(10) Patent No.: US 7,830,504 B2
Deppermann et al.　　(45) Date of Patent: Nov. 9, 2010

(54) AUTOMATED SYSTEMS AND ASSEMBLIES FOR USE IN EVALUATING AGRICULTURAL PRODUCTS AND METHODS THEREFOR

(75) Inventors: Kevin L. Deppermann, St. Charles, MO (US); Steven H. Modiano, Manchester, MO (US); Cynthia L. Ludwig, St. Louis, MO (US); Brad D. White, Creve Coeur, MO (US); Beth J. Calabotta, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 225 days.

(21) Appl. No.: 12/275,008

(22) Filed: Nov. 20, 2008

(65) Prior Publication Data

US 2009/0161102 A1　　Jun. 25, 2009

Related U.S. Application Data

(60) Provisional application No. 60/989,245, filed on Nov. 20, 2007.

(51) Int. Cl.
*G01J 3/42*　　(2006.01)
(52) U.S. Cl. .................... 356/305; 356/328; 382/110
(58) Field of Classification Search ............... 356/305, 356/328; 382/110
See application file for complete search history.

(56) References Cited

U.S. PATENT DOCUMENTS

| | | | |
|---|---|---|---|
| 3,861,788 A | 1/1975 | Webster | |
| 4,037,970 A | 7/1977 | Webster et al. | |
| 4,040,747 A | 8/1977 | Webster | |
| 4,260,262 A | 4/1981 | Webster | |
| 4,734,584 A | 3/1988 | Rosenthal | |
| 4,752,689 A | 6/1988 | Satake | |
| 5,132,538 A | 7/1992 | Norris | |

(Continued)

FOREIGN PATENT DOCUMENTS

EP　　0 636 310 A1　　2/1995

(Continued)

OTHER PUBLICATIONS

Winfield et al., "A Column Elutriator for Extracting Cyst Nematodes and Other Small Invertebrates from Soil Samples", Annals of Applied Biology, vol. 111, No. 1, 1987, pp. 223-232.

(Continued)

*Primary Examiner*—F. L Evans
(74) *Attorney, Agent, or Firm*—James E. Davis; Joseph A. Schaper; Harness, Dickey & Pierce, P.L.C.

(57) ABSTRACT

Methods and assemblies are provided for evaluating plants for presence of pests. Methods may include separating pests from a plant to produce a sample of pests for analysis, illuminating the sample to produce emitted light from the sample, and comparing the emitted light from the sample to a model to discriminate pests within the sample. Assemblies may include a separating unit operable to separate pests from a plant to produce a sample comprising pests, a light source for illuminating at least part of the sample, and an imaging device adjacent the light source for receiving light from the illuminated sample and creating an image of the sample.

41 Claims, 27 Drawing Sheets

U.S. PATENT DOCUMENTS

| | | | |
|---|---|---|---|
| 5,475,221 | A | 12/1995 | Wang |
| 5,533,145 | A | 7/1996 | Shofner et al. |
| 5,668,374 | A | 9/1997 | DiFoggio et al. |
| 5,751,421 | A | 5/1998 | Wright et al. |
| 5,918,977 | A | 7/1999 | Borggaard et al. |
| 5,991,025 | A | 11/1999 | Wright et al. |
| 6,096,944 | A | 8/2000 | Vierling et al. |
| 6,100,526 | A | 8/2000 | Mayes |
| 6,646,264 | B1 | 11/2003 | Modiano et al. |
| 6,706,989 | B2 | 3/2004 | Hunter et al. |
| 6,809,819 | B1 | 10/2004 | Vinjamoori et al. |
| 7,123,750 | B2 | 10/2006 | Lu et al. |
| 7,367,155 | B2 | 5/2008 | Kotyk et al. |
| 7,403,855 | B2 | 7/2008 | Fuessley et al. |
| 2001/0014750 | A1 | 8/2001 | Ulrich et al. |
| 2003/0142852 | A1 | 7/2003 | Lu et al. |
| 2004/0160607 | A1 | 8/2004 | Lin et al. |
| 2005/0082207 | A1 | 4/2005 | Deppermann |
| 2006/0006335 | A1 | 1/2006 | Lawrence et al. |
| 2006/0042528 | A1 | 3/2006 | Deppermann |
| 2007/0207485 | A1 | 9/2007 | Deppermann et al. |
| 2007/0240242 | A1 | 10/2007 | Modiano et al. |
| 2008/0113367 | A1 | 5/2008 | Becker et al. |
| 2008/0131254 | A1 | 6/2008 | Cope et al. |
| 2008/0131924 | A1 | 6/2008 | Cope et al. |
| 2008/0243392 | A1 | 10/2008 | Fuessley et al. |
| 2008/0310674 | A1 | 12/2008 | Modiano et al. |
| 2008/0317279 | A1 | 12/2008 | Deppermann et al. |
| 2009/0032441 | A1 | 2/2009 | Corak et al. |

FOREIGN PATENT DOCUMENTS

| | | |
|---|---|---|
| EP | 0 511 184 B1 | 6/1998 |
| EP | 0 539 537 B2 | 12/2000 |
| WO | WO 96/24830 | 8/1996 |
| WO | WO 98/44140 | 10/1998 |
| WO | WO 99/40419 | 8/1999 |
| WO | WO 99/58959 | 11/1999 |
| WO | WO 00/71993 A1 | 11/2000 |
| WO | WO 01/89288 A1 | 11/2001 |
| WO | WO-02/071040 A2 | 9/2002 |
| WO | WO-2006/026467 A2 | 3/2006 |

OTHER PUBLICATIONS

Been et al., "A Scaled-up Seinhorst Elutriator for Extraction of Cyst Nematodes from Soil", Nemtology, vol. 9, No. Part 3, Mar. 2007, pp. 431-435.

"Soybean Cyst Nematode", Plant Pathology, Iowa State University, University Extension, Ames, Iowa, Pm-879, Revised Oct. 1995, 6 pages.

"Seed Meister Luminar 3076", Brimose Corporation of America, Baltimore, MD, http://www.brimrose.com/seed_meister.html Mar. 27, 2007.

P.A. Hailey—Pfizer Central Research, "The Role of NIR Spectroscopy in the Measurement of Pharmaceutical Manufacture", http://www.brimrosecom/hailey.html, Mar. 27, 2007.

Dr. Jolanta Soos, "Industrial Process Monitoring Requires Rugged AOTF Tools", *Laser Focus World*, Aug. 1994.

"Rapid Identification of Organic Contaminants in Retreated Waste Water Using AOTF near-IR Spectrometry", *ISA 1995 Meeting Proceedings*, pp. 87-95, 1995.

Archibald et al., "Development of Short-Wavelength Near-Infrared Spectral Imaging for Grain Color Classification," SPIE vol. 3543, 1998, pp. 189-198.

Daun et al., "Comparison of Three Whole Seed Near-Infrared Analyzers for Measuring Quality Components of Canola Seed", vol. 71, No. 10, 1994, pp. 1063-1068.

Delwiche, "Single Wheat Kernel Analysis by Near-Infrared Transmittance: Protein Content," Analytical Techniques and Instrumentation, vol. 72, No. 1, 1995, pp. 11-16.

Dowell, "Automated Color Classification of Single Wheat Kernels Using Visible and Near-Infrared Reflectance," Cereal Chemistry, vol. 75(1), 1998, pp. 142-144.

Dowell et al., "Automated Single Wheat Kernel Quality Measurement Using Near-Infrared Reflectance," ASAE Annual International Meeting, 1997, paper No. 973022.

Massie and Norris, "Spectral Reflectance and Transmittance Properties of Grain in the Visible and Near Infrared", Transactions of the ASAE, Winter Meeting of the American Society of Agricultural Engineers, 1965, pp. 598-600.

Orman and Schumann, "Comparison of Near-Infrared Spectroscopy Calibration Methods for the Prediction of Protein, Oil, and Starch in Maize Grain," J. Agric. Food Chem. vol. 39, 1991, pp. 883-886.

Robutti, "Maize Kernel Hardness Estimation in Breeding by Near-Infrared Transmission Analysis," Analytical Techniques and Instrumentation vol. 72, No. 6, 1995, pp. 632-636.

136

AUTOMATED SYSTEMS AND ASSEMBLIES FOR USE IN EVALUATING AGRICULTURAL PRODUCTS AND METHODS THEREFOR

CROSS-REFERENCE TO RELATED APPLICATION

This application claims the benefit of U.S. Provisional Application No. 60/989,245, filed on Nov. 20, 2007, the entire disclosure of which is incorporated herein by reference.

FIELD

The present disclosure relates generally to systems and assemblies for use in evaluating agricultural products, and more particularly to an automated processing assembly and imaging system for use in determining and/or quantifying pest presence, infestation, and the like in agricultural products.

BACKGROUND

The statements in this section merely provide background information related to the present disclosure and may not constitute prior art.

Pests can cause extensive damage to agricultural crops. Pesticides are available to control some pest infestations. But in other infestations, pests may be resistant to pesticides. For example, soybean cyst nematodes can infiltrate and infest in soybean crops. And once soybean cyst nematode cysts are present in the soil of the crops, they are persistent and often difficult, if not impossible, to remove (e.g., with pesticides).

One approach to curb the damage caused by persistent pests is to create varieties of plants that are more resistant to the pests than other varieties. However, breeding for these enhanced plant varieties typically requires analysis of large numbers of plant and soil samples in order to determine which varieties have developed resistant properties. A current method for analyzing plants (e.g., soybean plants) includes manually counting pests (e.g., soybean cyst nematode cysts) from each sample plant. But as can be appreciated, manual counting of pests for a large number of sample plants can be extremely slow, cumbersome, and resource intensive. Moreover, accuracy of analysis may be a concern. Accordingly, it would be desirable to provide an automated system for such analysis.

SUMMARY

This section provides a general summary of the disclosure, and is not a comprehensive disclosure of its full scope or all of its features.

Example embodiments of the present disclosure generally relate to methods for evaluating plants for presence of pests. Example methods may generally include separating pests from a plant to produce a sample of pests for analysis, illuminating the sample to produce emitted light from the sample, and comparing the emitted light from the sample to a model to discriminate pests within the sample.

Example embodiments of the present disclosure also generally relate to assemblies for evaluating plants for presence of pests. Example assemblies may generally include a separating unit operable to separate pests from a plant to produce a sample comprising pests, a light source for illuminating at least part of the sample, and an imaging device adjacent the light source for receiving light from the illuminated sample and creating an image of the sample.

Example embodiments of the present disclosure also generally relate to methods for quantifying soybean cyst nematode infestation on a soybean plant. Example methods may generally include providing at least one soybean plant having soybean cyst nematodes, separating soybean cyst nematode cysts from the plant to prepare a sample comprising at least soybean cyst nematode cysts, illuminating the sample to produce light of mixed wavelengths emitted from at least one discrete spatial sample point of the sample, comparing wavelengths of the emitted light to a model to discriminate soybean cyst nematode cysts within the sample, and calculating the quantity of soybean cyst nematode cysts in the sample.

Example embodiments of the present disclosure also generally relate to methods of evaluating pest resistance in plants. Example methods may generally include harvesting one or more plants comprising pests, separating the pests from the plant to prepare a sample comprising pests, illuminating the sample to produce emitted light from the sample, and comparing the emitted light from the sample to a model to discriminate pests within the sample.

Further areas of applicability will become apparent from the description provided herein. It should be understood that the description and specific examples are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
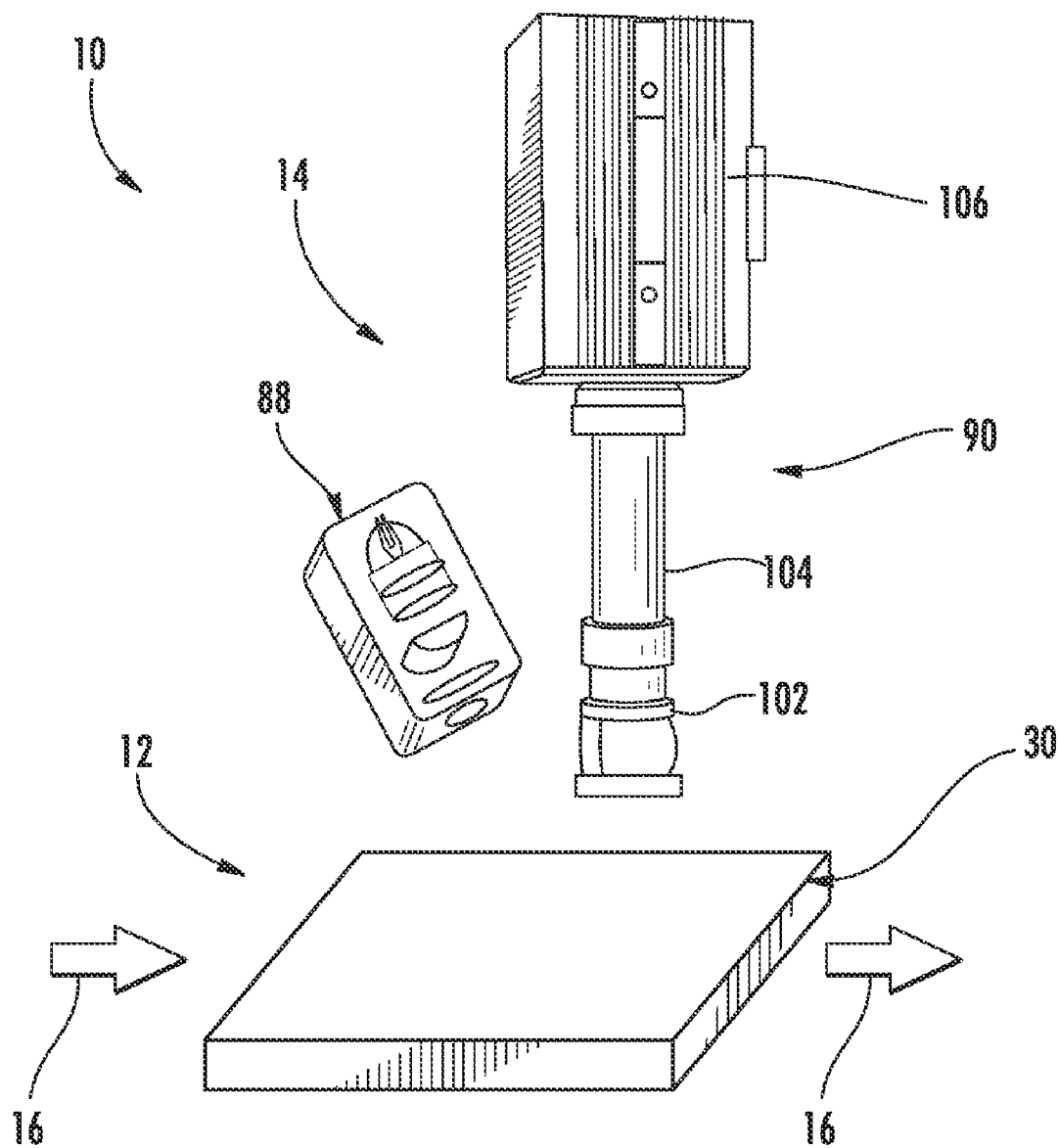
FIG. 1 is a perspective view schematically illustrating an example embodiment of an automated system for use in analyzing agricultural products.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference now to the drawings, and particularly to FIG. 1, an example embodiment of an automated analysis system, assembly, etc. for use in analyzing agricultural products is schematically shown generally at reference numeral 10. The illustrated analysis system 10 may be used, for example, for analyzing and/or determining the quantity of pests in samples of the agricultural products. Images of the samples may be compared to known values to determine identity, quantity, etc. of pests present in the samples. It is understood that one or more sample may be analyzed in the illustrated analysis system 10.

The analysis system 10 generally includes a sample carrier 12 and an imaging assembly 14. The sample carrier 12 is configured for holding and for moving samples of the agricultural products through a field of view of the imaging assembly 14 for analysis. Arrows 16 indicate an example direction of movement of the sample carrier 12 relative to the imaging assembly 14. In other example embodiments, analysis systems may include imaging assemblies moveable relative to sample carriers for analysis.

In the illustrated analysis system 10, agricultural products may include, for example, soybean plants; and agricultural samples prepared from soybean plants may include, for example, Heterodera glycines (soybean cyst nematodes). The samples may also include soil matter, root portions, other plant matter, etc. In other example embodiments, agricultural products may include one or more of corn plants, bean plants, clover plants, oat plants, beet plants, crucifers, spinach plants, tomato plants, eggplant plants, vetch, lespedeza, lupine, 'weedy' legumes, etc. In still other example embodiments, agricultural samples may include other pests, infestations, pathogen infections, other botanical conditions or characteristics, etc., including, for example: corn ear mold on corn plants; *Heterodera* glycines (soybean cyst nematodes) on common bean plants, vetch, lespedeza, lupine, 'weedy' legumes, etc.; *Heterodera trifolii* on clover plants; *Heterodera avenae* on cereals (like oat plants); *Heterodera schachtii* on sugar beet plants, crucifers, and spinach plants; *Globodera rostochiensis* on tomato plants and eggplant plants; *Meloidogyne incognita* on soybean plants, tomato plants, etc.; etc.

The soybean plants used to prepare the agricultural samples for use in the illustrated analysis system 10 may be grown under generally controlled conditions, for example in a greenhouse. For example, in one embodiment, soybean seeds are planted in marked (e.g., bar-coded, etc.) pots containing, for example, sterilized river wash sand as planting media/matter. The seeds are cultivated and allowed to germinate. Following germination, the soybean plants are inoculated with soybean cyst nematode eggs of a desired race. Inoculation may include, for example, delivering about two thousand soybean cyst nematode eggs into each of the soybean plant pots. The infected soybean plants are cultivated for about thirty days following inoculation and are then harvested for analysis. In other example embodiments, inoculation may include, for example, delivering any desired number of soybean cyst nematode eggs into soybean plant pots. For example, about two-hundred soybean cyst nematode eggs may be delivered.

The agricultural samples may be generally prepared by removing, or separating, the planting media and soybean cyst nematodes from roots of the harvested soybean plants. This may be done, for example, by washing, or rinsing, the planting media and soybean cyst nematodes from the roots with, for example, water or any other suitable washing medium, and filtering the washed material. The sample generally comprises the dried filtered material, which may include: soybean cyst nematode eggs, larvae, or cysts; soil material; root material; etc. The agricultural samples may be prepared manually or at least partly by automated systems, apparatus, assemblies, etc. For example in one example embodiment, an automated system may be used to inoculate soybean plants with soybean cyst nematode eggs. In another example embodiment, an automated system may be used to cultivate and/or harvest the soybean plants. In still another example embodiment, an automated system may be used to remove planting media from roots of soybean plants to prepare samples. Other example embodiments may include one or more combination of these automated systems. In still other example embodiments, plants may be grown and/or inoculated with pests differently than described herein. In addition, samples may be prepared from the plants differently than described without departing from the scope of the invention. An example automated system, apparatus, etc. operable to separate plant materials (e.g., separate, remove, etc. planting media from roots of plants, etc.) and suitable for use with the analysis system 10 will be described hereinafter.

Figure 2A:
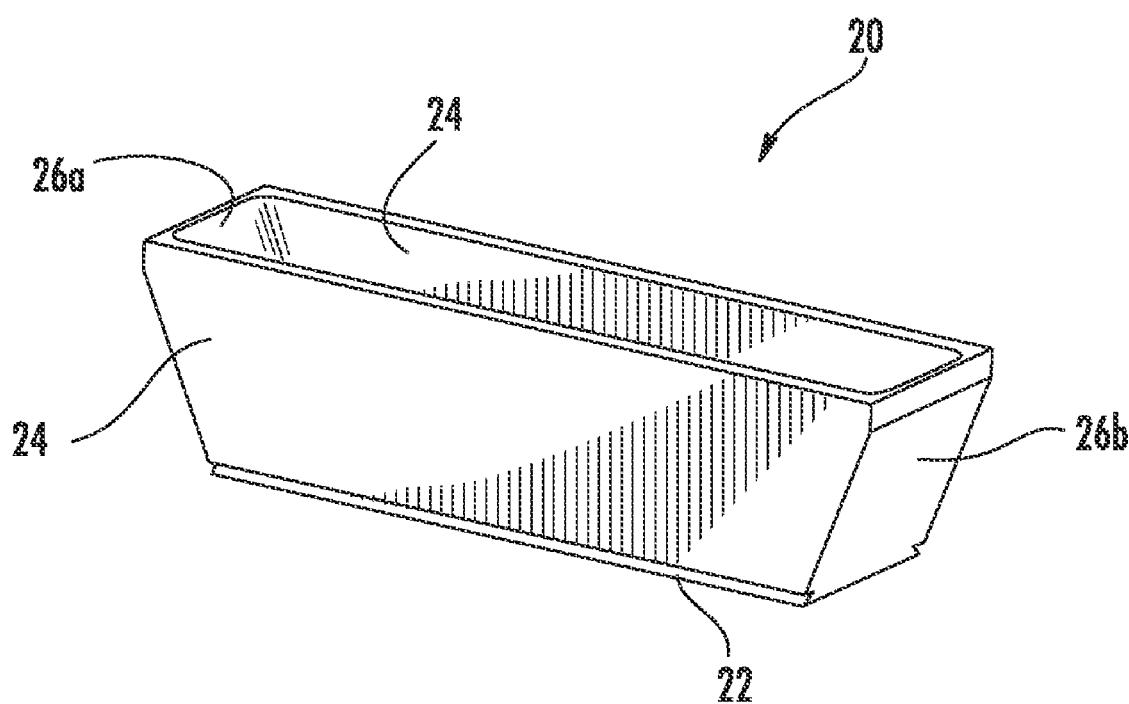
FIG. 2A is a perspective view of an example cuvette for holding samples of agricultural products during analysis.
Figure 2B:
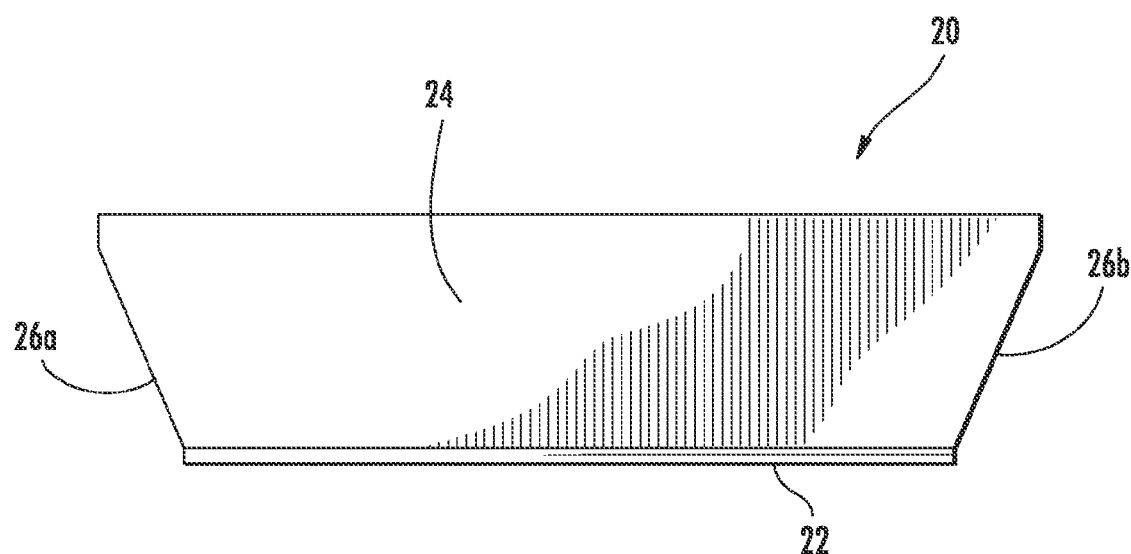
FIG. 2B is a side elevation view of the cuvette of FIG. 2A.
Figure 3:
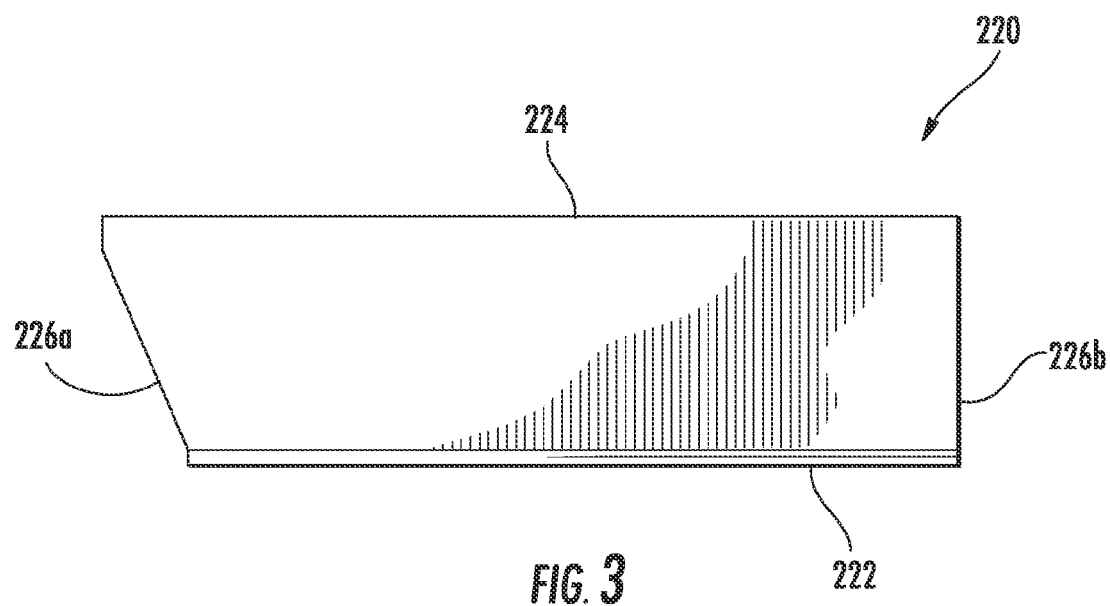
FIG. 3 is a side elevation view of an alternative example embodiment of a cuvette.

The filtered planting media and soybean cyst nematodes removed from the roots of the soybean plants may be transferred to one or more cuvettes for analysis after drying. An example cuvette 20 is shown in FIGS. 2A and 2B. The cuvette 20 is generally rectangular in shape when viewed in plan, and generally trapezoidal in shape when viewed in elevation. The cuvette 20 includes a bottom wall 22, two generally opposing side walls (each designated 24), and two generally opposing end walls 26a and 26b that define a volume for receiving an agricultural sample in the cuvette 20. Both end walls 26a and 26b (as viewed in FIGS. 2A and 2B) extend generally outward at an angle from the bottom wall 22. FIG. 3 illustrates an alternative example embodiment of a cuvette 220 capable of being used with the analysis system 10. In this embodiment, the cuvette 220 includes side walls 224, a left end wall 226a (as viewed in FIG. 3) that extends generally outward at an angle from a bottom wall 222, and a right end wall 226b that extends upward generally perpendicularly from the bottom wall 222.

In the illustrated analysis system 10, the cuvettes 20 are formed from a material that helps differentiate the cuvette from pest material, plant material, soil material, etc. during spectral analysis. In other example embodiments, a system may include one or more cuvettes formed from an opaque material and/or a translucent or transparent material for reflectance analysis and/or transmission analysis.

Figure 4:
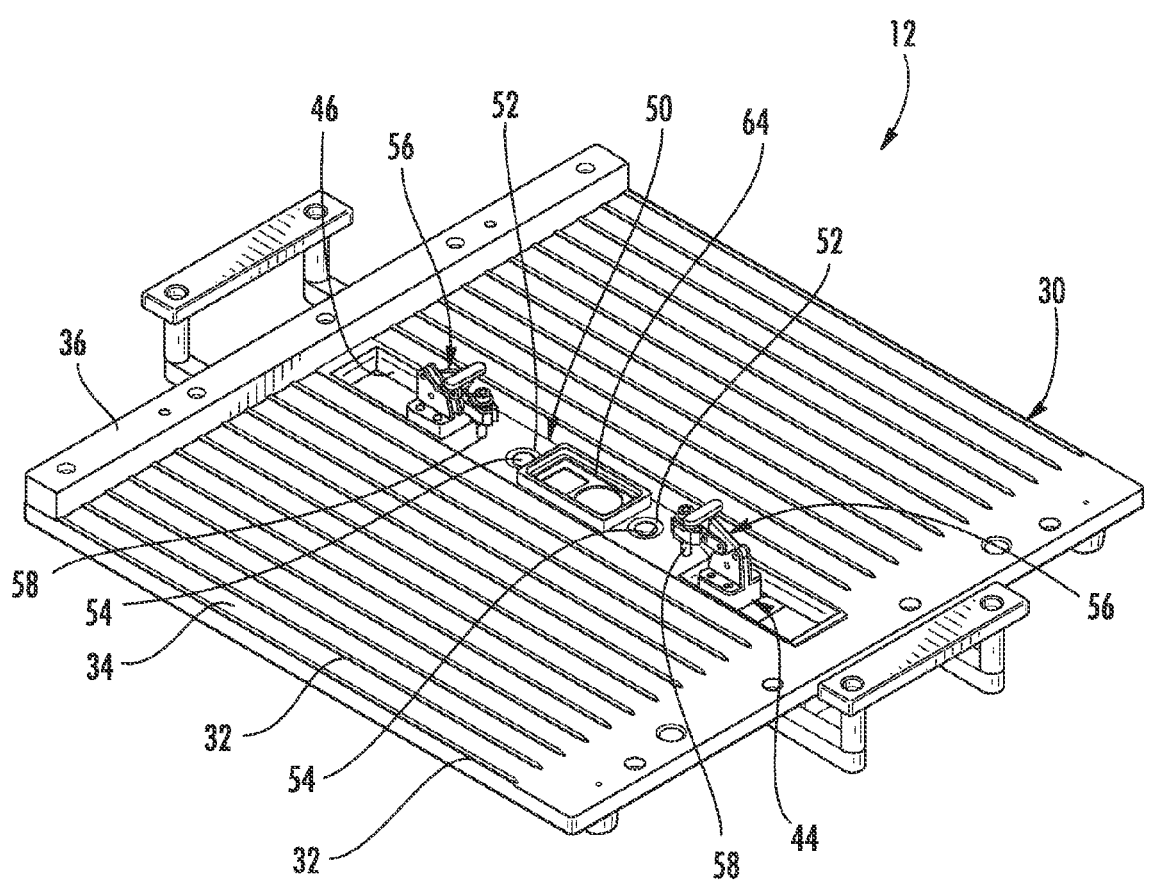
FIG. 4 is a perspective view of a sample carrier of the automated system.
Figure 5:
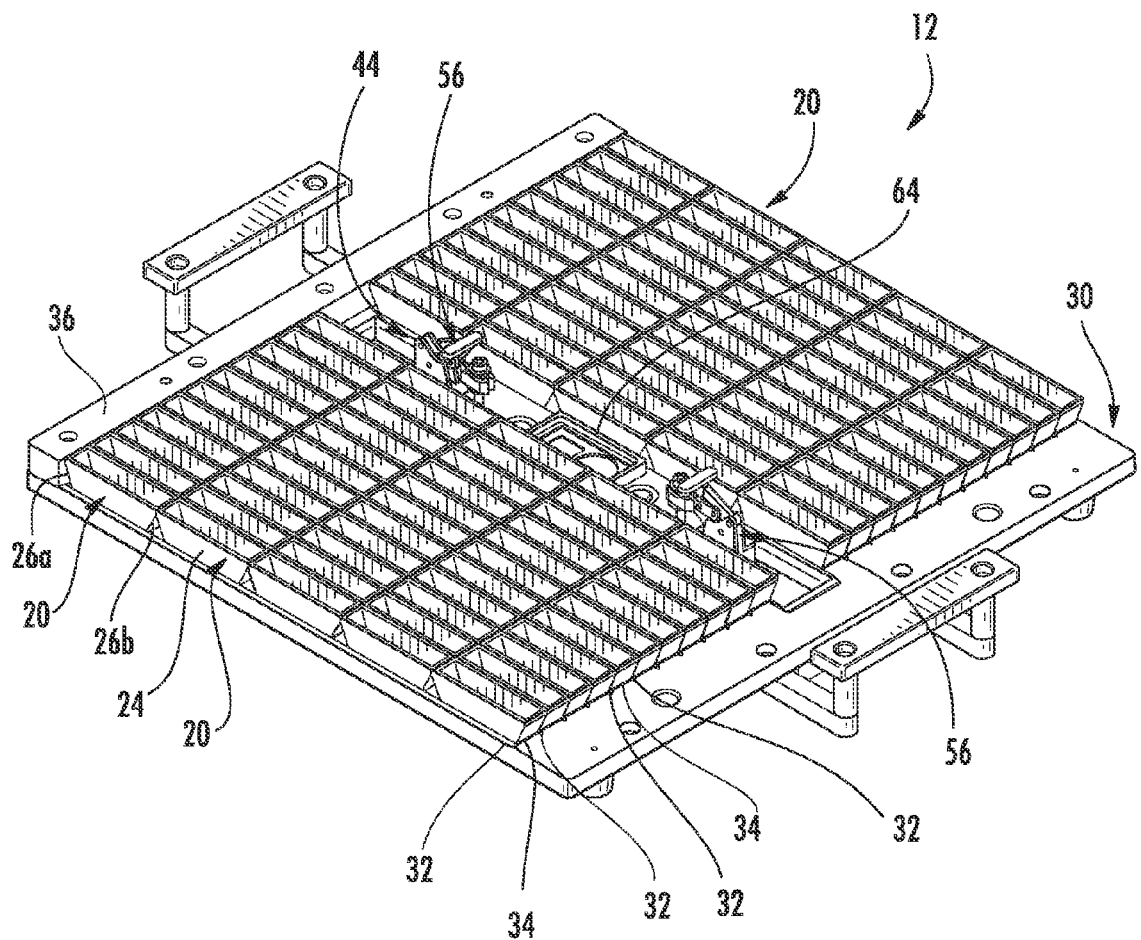
FIG. 5 is a perspective view similar to FIG. 4 with cuvettes inserted onto the sample carrier.
Figure 6:
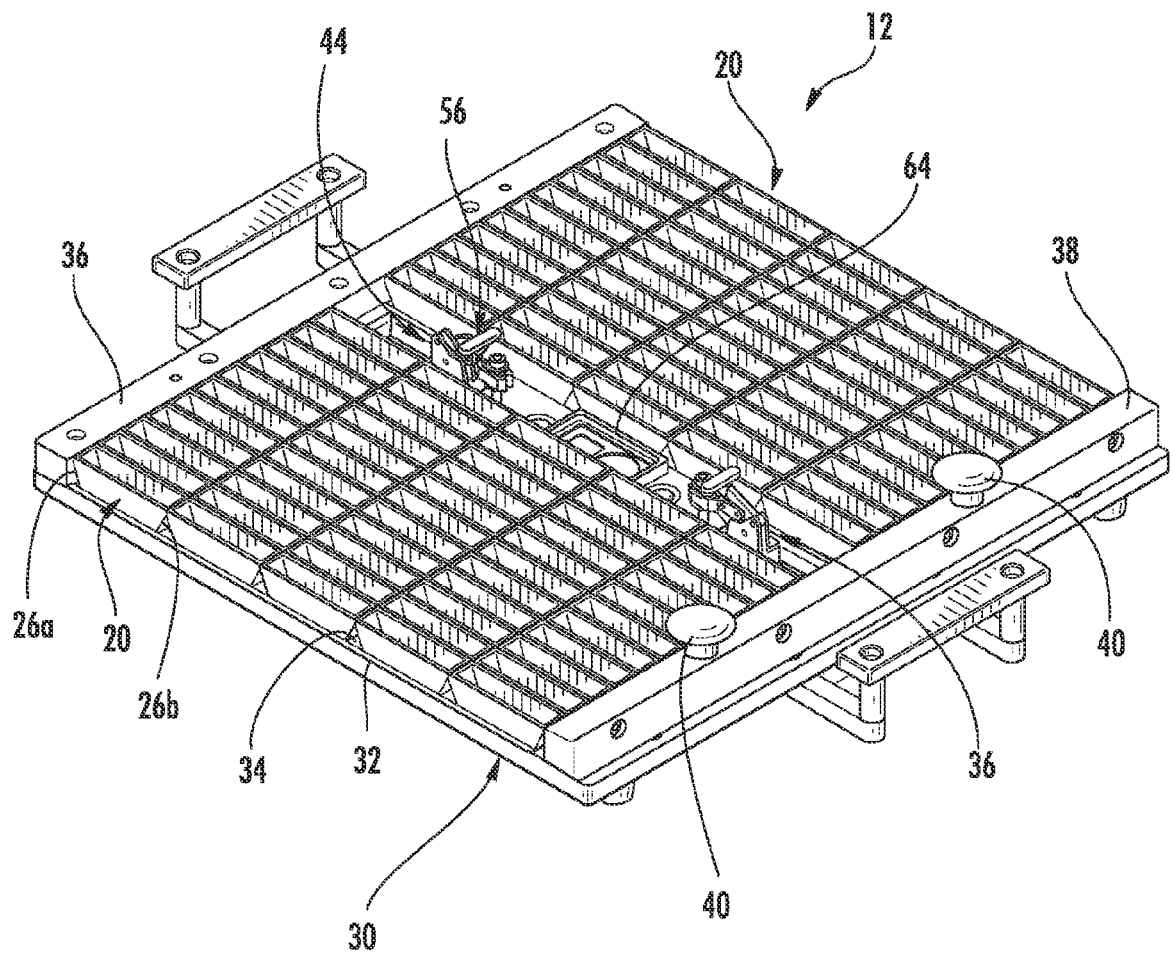
FIG. 6 is a perspective view similar to FIG. 5 with a compression bar connected to the sample carrier for helping retain the cuvettes on the sample carrier.

With reference to FIGS. 4-6, the sample carrier 12 includes a stage for receiving the cuvettes 20 (FIGS. 5 and 6) and for moving the cuvettes 20 received thereon relative to the imaging assembly 14. The stage 30 is disposed in a generally horizontal orientation for supporting the cuvettes 20. As shown in FIG. 4, upstanding guides 32 extend generally along a width of the stage 30 and define channels 34 for receiving the cuvettes 20 therein on the stage. As shown in FIG. 5, the guides 32 are configured to engage the opposing side walls 24 of each cuvette 20 for securing each cuvette between the guides within the respective channel 34. Cuvettes 20 may be slid lengthwise into each channel 34 such that an angled (left) end wall 26a of a first cuvette 20 in each channel generally abuts an end stop 36 of the stage 30. As shown in FIG. 6, a compression bar 38 is securable to the stage 30 generally opposite the end stop 36 to prevent the cuvettes 20 from sliding or moving out of the channels 34 and off the stage 30 during operation. Threaded screws 40 extend through the compression bar 38 and engage the stage 30 to releasably secure the compression bar 38 to the stage 30. In the illustrated sample carrier 12, the stage 30 includes twenty-four channels 34 formed along a length of the stage. The channels 34 are each sized to receive five cuvettes 20 such that the stage 30 is capable of receiving a total of one hundred and ten cuvettes. Alternatively, the sample carrier 12 may receive the cuvette 220 illustrated in FIG. 3. Here, the channels 34 may each receive six of the cuvettes 220 such that the stage 30 may receive a total of one hundred and thirty-two cuvettes.

Figure 7:
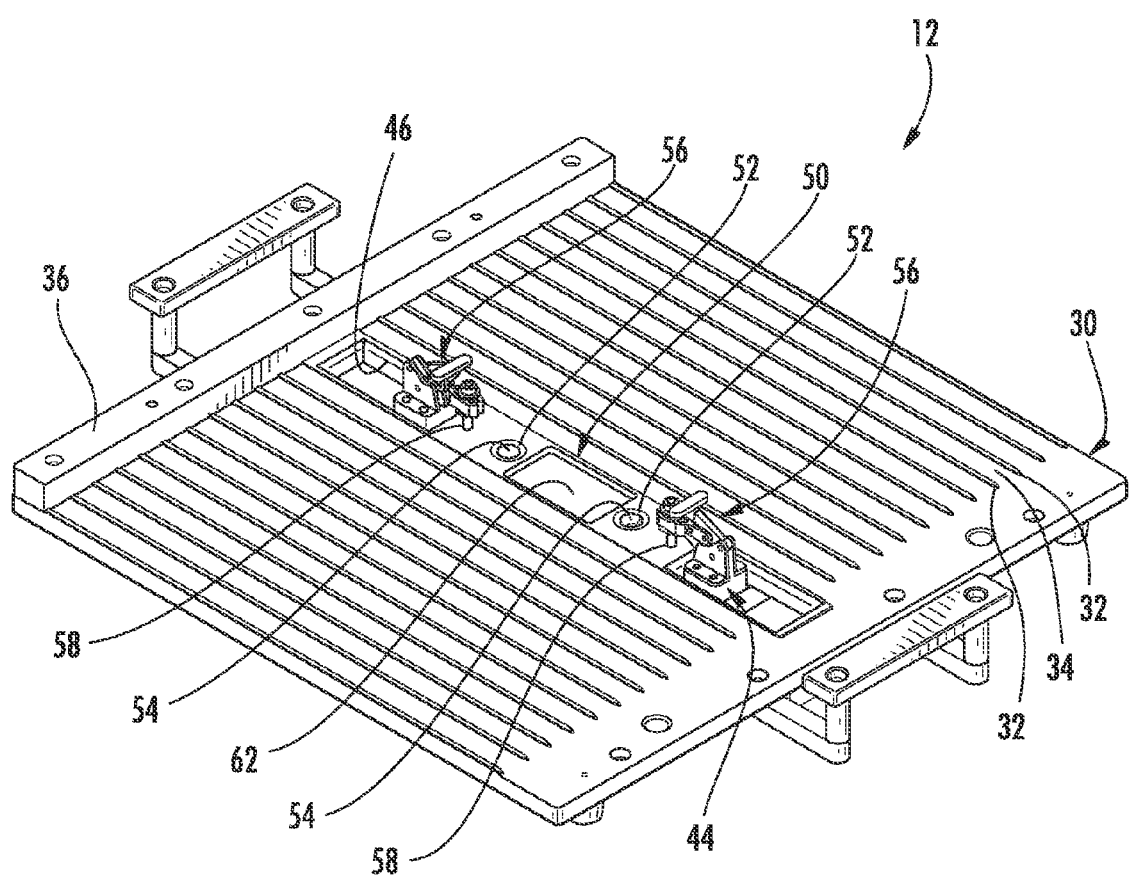
FIG. 7 is a perspective view similar to FIG. 4 with an imaging calibration block removed from the sample carrier to illustrate a connection plate and mounted on the sample carrier and a tray mounted on the connector plate.
Figure 8:
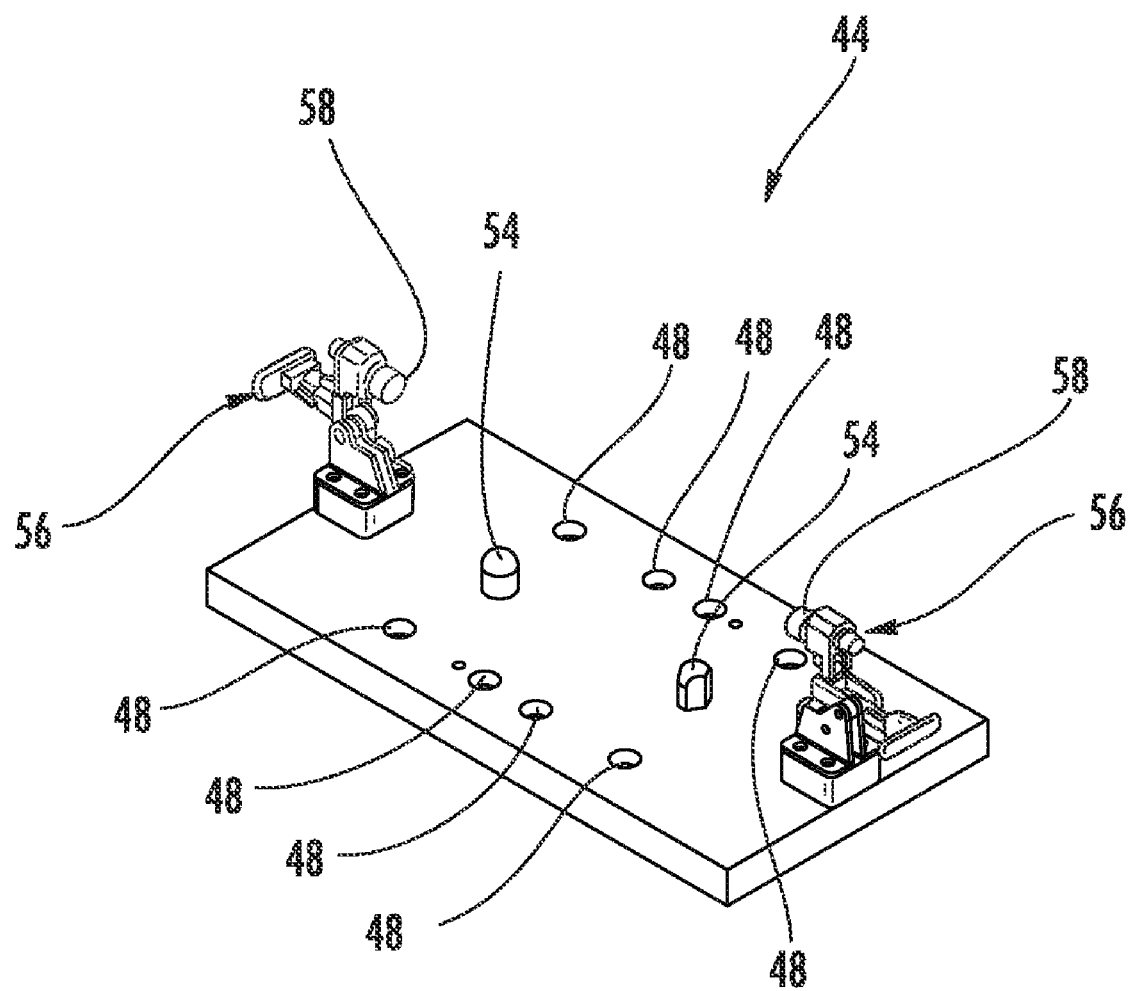
FIG. 8 is a perspective view of the connector plate.

With reference now to FIGS. 7 and 8, a connector plate 44 is disposed within a central opening 46 of the stage 30. The stage opening 46 extends generally along the width of the stage 30 for allowing movement of the connector plate 44 therealong. The connector plate 44 includes openings 48 along each lateral edge (FIG. 8). The openings 48 are configured for receiving connecting structure (not shown) to slidably connect the connector plate 44 to the stage 30.

The connector plate 44 is configured to support a tray 50 on the stage 30 (FIG. 7). The tray 50 includes two openings 52 positioned toward generally opposing ends of the tray for receiving corresponding retention pins 54 of the connector plate 44. The pins 54 help accurately align the tray 50 on the connector plate 44 and at least partly retain the tray thereon. Swing clamps 56 positioned toward generally opposing ends of the connector plate 44 help secure the tray 50 on the connector plate. A head 58 of each clamp 56 may be pivoted into engagement with the tray 50 to further secure the tray on the connector plate 44.

With reference to FIGS. 4 and 7, the tray 50 includes a central well 62 configured to receive an imaging calibration block 64 within the well (FIG. 4). The imaging calibration block 64 may be used to normalize and/or calibrate a response of the imaging assembly 14 of the analysis system 10. For example, the calibration block 64 may include a material used to establish the accuracy of the wavelength scale used for analysis, and a reference sample similar to the samples being analyzed.

Figure 9:
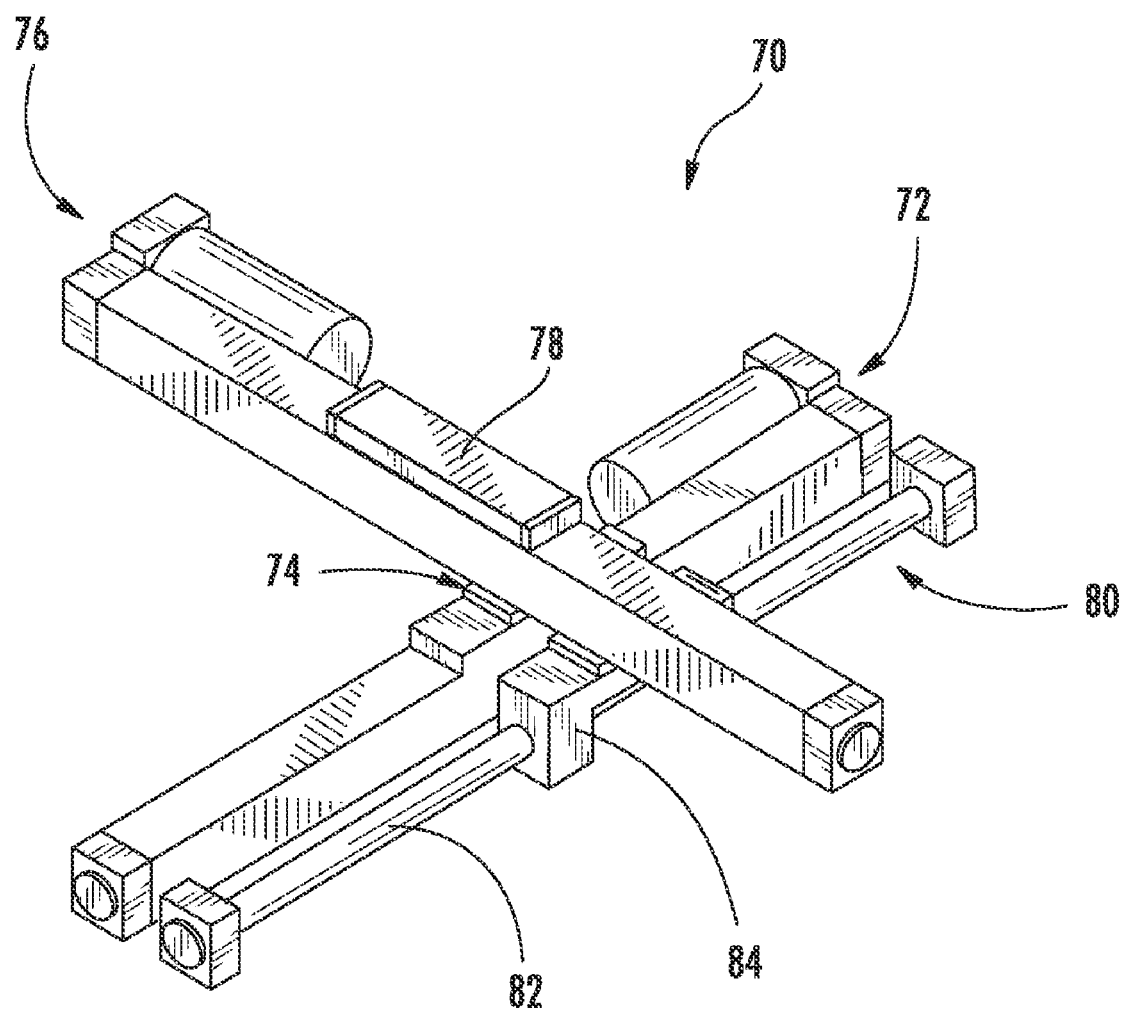
FIG. 9 is a perspective view schematically illustrating a translation mechanism of the sample carrier.

As previously stated, the sample carrier 12 (and more particularly the stage 30 thereof) is movable relative to the imaging assembly 14 for locating the cuvettes 20 and respective samples therein in the field of view of the imaging assembly 14. The sample carrier 12 also includes a translation mechanism 70 for use in moving the stage 30. FIG. 9 schematically illustrates an example two-dimensional translation mechanism 70 of the sample carrier 12 capable of moving the stage 30. The translation mechanism 70 includes a first linear actuator 72 having a first translatable carriage 74, and a second linear actuator 76 having a second carriage 78 generally mounted on the first carriage. A slider 80 having a rail 82 and a carriage 84 is positioned generally parallel to the first linear actuator 72. The stage 30 may be mounted on the second carriage 78, and thus moved precisely in two dimensions through the operation of the first and second linear actuators 72 and 76. In the illustrated embodiment, the translation mechanism 70 may be capable of moving the stage 30 in fine/small motion increments along the axis used for imaging so that the motion does not distort the image. In addition, the translation mechanism 70 may have low wobble and flutter specifications to minimize image distortions from slight wobble and flutter of the stage 30, cuvettes 20, and samples as they move past the imaging assembly 14.

With reference again to FIG. 1, the imaging assembly 14 generally includes a light source 88 positioned to direct light toward the samples in the sample carrier 12, and a light measuring device 90 positioned to receive light emitted from the samples. The light source 88 is configured to illuminate at least part of one or more of the samples. The light emitted by the samples generally includes mixed wavelengths emitted from one or more discrete spatial sample points of the illuminated portion of the samples. The light measuring device 90 characterizes the intensity of one or more wavelengths of the emitted light from each of the sample points and produces an image of the sample that can be used for further analysis.

In the illustrated analysis system 10, the light source 88 is capable of illuminating the samples with light comprising wavelengths generally between about 450 nanometers and about 900 nanometers. This produces emitted light from the samples comprising wavelengths also generally between about 450 nanometers and about 900 nanometers. In other example embodiments, light sources may illuminate samples with light comprising wavelengths less than about 450 nanometers and/or light comprising wavelengths greater than 900 nanometers; with light in the visible spectral region, near infrared spectral region, ultra-violet spectral region, mid-infrared region, combinations thereof, etc.

Also in the illustrated analysis system 10, the light source 88 is positioned on the same side of the sample carrier 12 as the light measuring device 90 such that light emitted by the samples is generally light from the light source 88 reflected by the samples. In other example embodiments, light sources and light measuring devices may be positioned on generally opposite sides of sample carriers such that light emitted by samples is generally light transmitted through the samples. Accordingly, it should be understood that emitted light may include light reflected from the samples, cuvettes, and/or sample carrier, and/or light transmitted through the samples, cuvettes, and/or sample carrier. Imaging assemblies are further described in co-owned U.S. Pat. No. 6,646,264 (Modiano et al.), the entire disclosure of which is incorporated herein by reference.

The light source 88 and light measuring device 90 may be oriented relative to the sample carrier 12 to optimize collection of diffusely scattered light emitted from the samples on the carrier 12. For example in the illustrated embodiment, the light source 88 is positioned at an angle of about twenty degrees from a vertical line, and the light measuring device 90 is positioned at an angle of about twenty degrees from the vertical line opposite the light source 88 and about forty degrees from the light source. At this orientation, light from the light source 88 will be reflected from the sample to the light measuring device 90.

Figure 10:
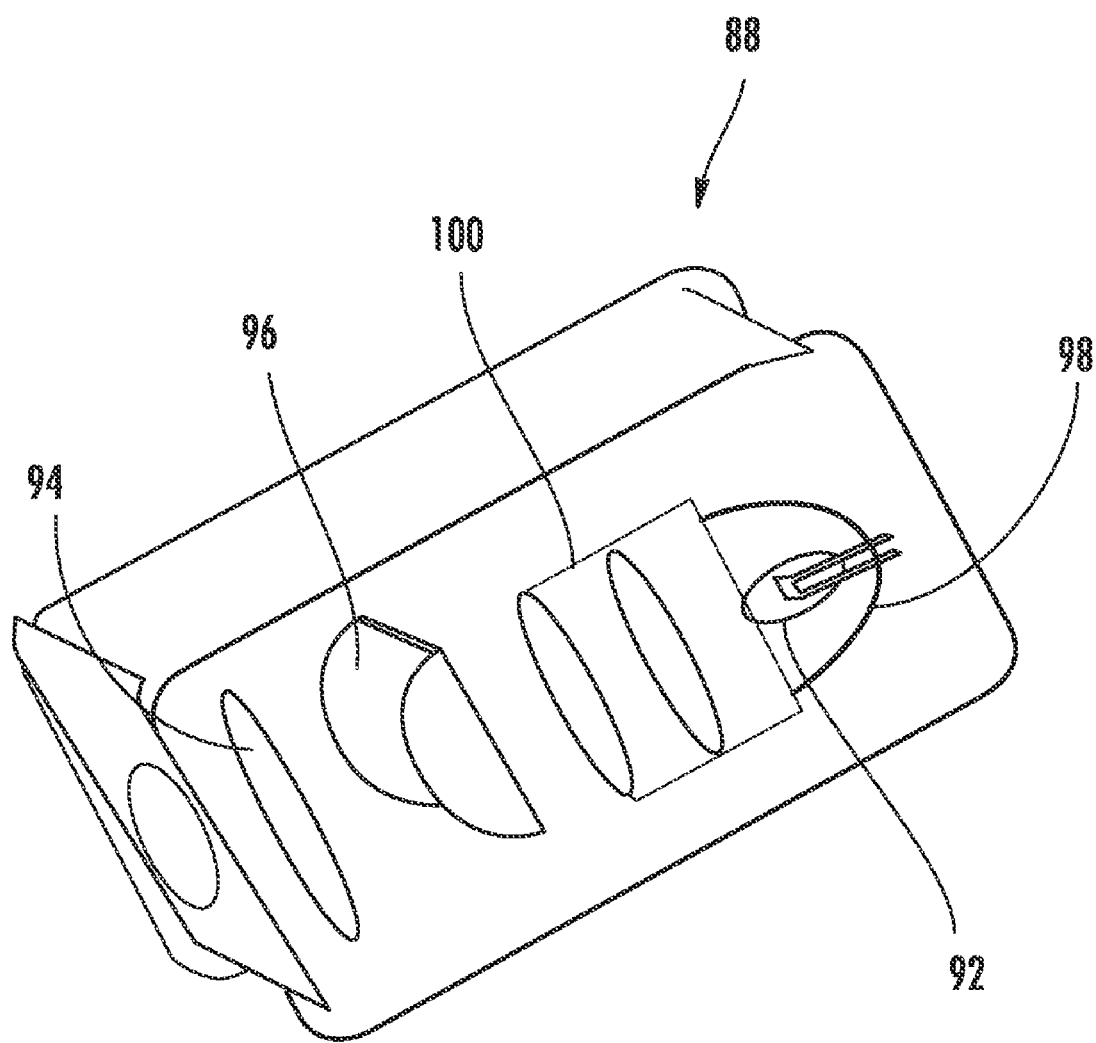
FIG. 10 is a perspective view schematically illustrating a light source of the automated system.

FIG. 10 schematically illustrates the example light source 88. As illustrated, the light source 88 generally includes a lamp 92 for providing continuous broadband light to illuminate the samples and a forward filter 94 for removing unwanted light from impinging on the illuminated sample. A cylindrical lens 96 rearward of the filter 94 focuses the light from the lamp 92 onto the samples. In the illustrated light source 88, the lens 96 focuses the light into a beam shaped as a thin line that extends across a width of at least part of one or more of the samples for use by the imaging assembly 14 in line scanning incremental portions of the samples. An integral parabolic reflector 98 and condenser optics 100 may also be included in the light source 88. In other example embodiments, systems may include light sources with lamps including, for example, quartz tungsten halogen lamps, halogen lamps, tungsten halogen lamps, long filament halogen lamps, xenon lamps, xenon flash lamps, fluorescent lamps, neon lamps, mercury lamps, etc.

Figure 11:
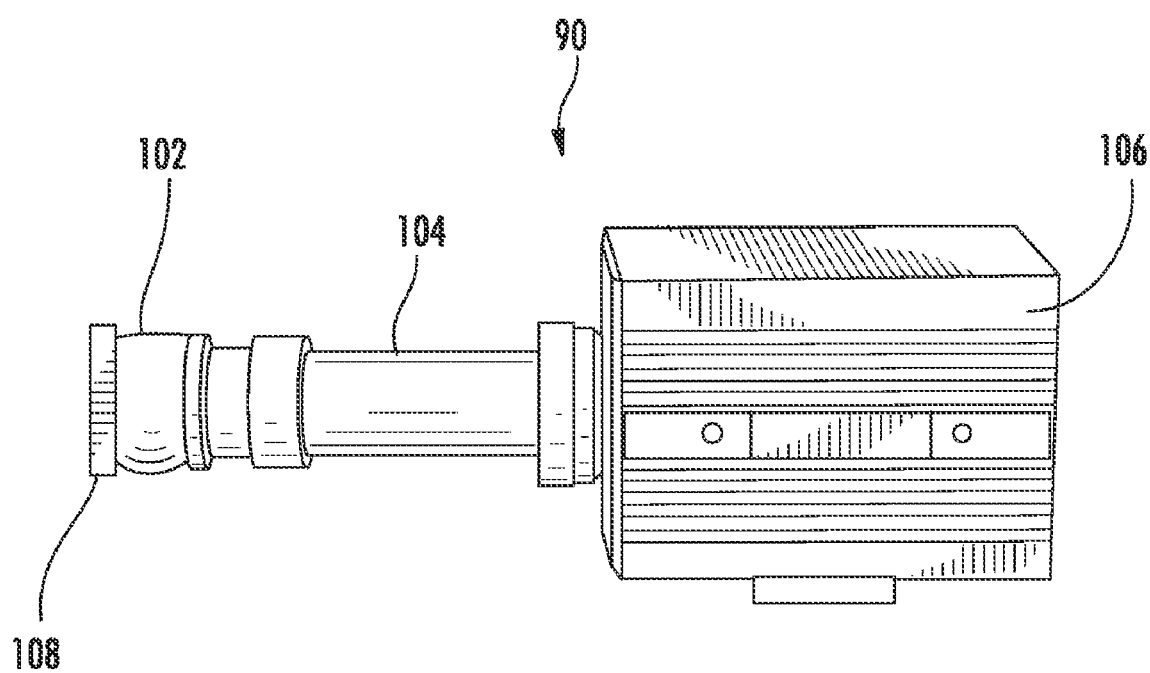
FIG. 11 is a perspective view schematically illustrating a light measuring device of the automated system.

The light measuring device 90 of the illustrated analysis system 10 is schematically shown in FIG. 11 and generally includes an imaging lens 102 for receiving light emitted by the samples along the line of light produced by the light source 88, a spectrograph 104 connected to the imaging lens 102 for dispersing or separating the received light into component wavelengths, and a camera 106 connected to the spectrograph 104 for producing an image from the component wavelengths.

The imaging lens 102 includes an electronically actuated shutter 108 that selectively closes to block light from passing to the lens (and to the spectrograph 104 and camera 106) for collecting a dark image used in correcting images of the samples produced by the camera 106. For example, before sample analysis begins in the automated analysis system 10, the imaging calibration block 64 may initially be moved by the sample carrier into the field of view of the imaging assembly 14 for system calibration. The light source 88 illuminates the calibration block 64, but the electronic shutter 108 initially blocks entrance of light to the spectrograph 104 and camera 106. Thus, a dark image is acquired which can be used for later use to calculate sample reflectance.

In some example systems, light measuring devices may include imaging lenses that also minimize parallax distortion and maintain generally constant magnification. For example, in one example embodiment an imaging lens includes about a 0.5 times magnification providing a field of view of about 17.6 millimeters, a working distance of about 120 millimeters, a depth of field of about 2.5 millimeters, and a spatial resolution of about 17,600 microns per 1,390 pixels, or about 13 microns. In this embodiment, the imaging lens is coated for the spectral range of interest to avoid chromatic aberrations.

Figure 12:
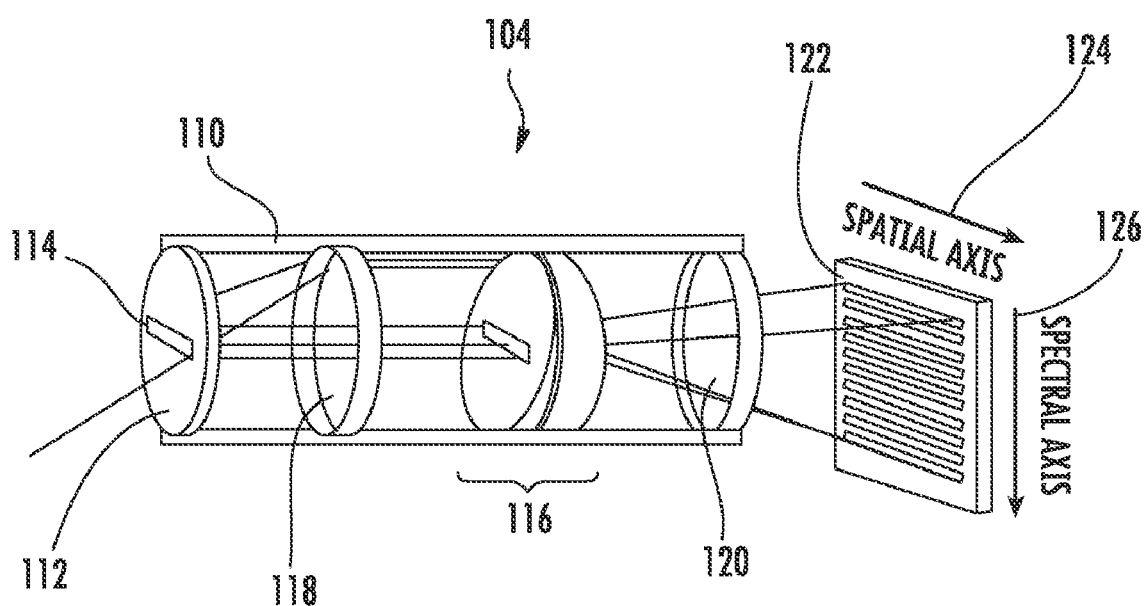
FIG. 12 is a perspective view schematically illustrating a spectrograph of the light measuring device.

As schematically shown in FIG. 12, the spectrograph 104 of the illustrated light measuring device 90 includes a straight axis imaging spectrograph with a generally tubular housing 110. A disc 112 with an entrance slit 114 therein is disposed in the housing 110 generally adjacent the imaging lens 102 (see, e.g., FIG. 11) for allowing light into the spectrograph 104. The disc 112 is oriented such that the entrance slit 114 is generally aligned with the line of light produced by the light source 88 on the samples so that a generally optimum amount of light emitted by the samples is received through the slit 114 into the spectrograph 104.

The spectrograph 104 also includes a prism/grating/prism (PGP) dispersing element 116 disposed between first and second interior lenses 118 and 120 for dispersing, or separating, light received into the spectrograph 104 into component wavelengths. The first interior lens 118 receives light from the entrance slit 114 and focuses it onto the PGP element 116. The PGP element then disperses the light into the component wavelengths and transmits the dispersed light through the second lens 120 (FIG. 12) to the camera 106. In the illustrated spectrograph 104, the PGP element 116 includes a volume-phase transmission grating that preferably provides good diffraction efficiency over a broad range of wavelengths. In one embodiment, for example, a PGP element includes grating that provides diffraction efficiency that is about 60 percent or greater at about 1,100 nanometers, and diffraction efficiency that is about 40 percent or greater at about 1,700 nanometers. In other example embodiments, spectrographs may include reflective grating having, for example, holographic grating or fixed groove grating.

With continued reference to FIG. 12, the component wavelengths of the light dispersed by the spectrograph 104 (and transmitted through the second lens 120 to the camera 106) are focused (or imaged) onto, for example, multiple datapoints (e.g., pixels, etc.) of a two-dimensional focal plane array 122 of the camera 106. The datapoints include discrete areas at which the component wavelengths of the corresponding light from each discrete spatial sample point of the samples may be detected. The component wavelengths for each discrete spatial sample point in a sample along the line of light produced by the light source 88 are generally focused on (or along) a horizontal spatial axis 124 of the focal plane array 122. The spectral information for each discrete spatial sample point in the sample along the line of light is dispersed along a vertical spectral axis 126 perpendicular to the spatial axis 124. The central component wavelength of dispersed light from each discrete spatial sample point in the sample goes generally straight through the spectrograph 104 to the focal plane array 122, while shorter and longer wavelengths are dispersed symmetrically above and below the central wavelength. After receiving the component wavelengths of the dispersed light from a sample, the camera 106 digitizes the wavelengths at each datapoint of the focal plane array 122 and forms a spectral image of the portion of the sample illuminated by the line of light from the light source 88. Each spectral image includes multiple component wavelengths from the multiple discrete spatial sample point in the sample being illuminated and analyzed.

The range of wavelengths of dispersed light transmitted by the spectrograph 104 to the camera 106 may be any range that is broad enough to allow analysis of the samples. For example in the illustrated embodiment, the spectrograph 104 may be capable of transmitting dispersed light having wavelengths in the range of about 450 nanometers to about 900 nanometers corresponding to the range of wavelengths produced by the light source 88 and emitted by the sample. In addition, the spectrograph 104 may have a spectral dispersion of about 50 nanometers per millimeter (nm/mm), and a spectral resolution of about 100 nanometers. In other example embodiments, spectrographs may be capable of transmitting dispersed light having wavelengths in a range different from those disclosed herein, for example, in ranges from about 100 nanometers up to about 2000 nanometers. In still other example embodiments, spectrographs may have spectral dispersions different than disclosed herein, for example, 100 nm/mm, 125 nm/mm, 150 nm/mm, etc. In still further example embodiments, spectrographs may have spectral resolutions different than described herein, for example, 50 nanometers, 40 nanometers, 30 nanometers, 20 nanometers, etc.

In the illustrated analysis system 10, the camera 106 may include a progressive scan charge coupled device (CCD) camera. The CCD camera may have a generally high spatial resolution and a spectral range of about 450 nanometers to about 900 nanometers. CCD cameras with other spectral ranges may be used within the scope of the invention (e.g., CCD cameras with spectral ranges extending below about 450 nanometers and/or above about 900 nanometers, etc.). In addition, CCD cameras may include, but are not limited to, Indium Antimonide (InAs) CCD cameras, Mercury Cadmium Telluride (MCT) CCD cameras, Platinum Silicide (PtSi) CCD cameras, Arsenic-doped Silicon (Si:As) CCD cameras, Indium Gallium Arsenide CCD cameras, etc. In one example embodiment, a format of a focal array for a CCD camera may be 320 by 240 pixels for a total of 76,800 detector pixels with a 40 micron pitch for each pixel. In this embodiment, the CCD camera may have an analog to digital accuracy of 12 bits, a pixel readout rate of 6.1 MHz, and a spectral response of 900 to 1,730 nanometers. Furthermore, the CCD camera may have a progressive scan video output allowing acquisition of one field per frame (e.g., frames per second, etc.) such that a spectral line image can be captured about every 16.67 milliseconds. In another embodiment, the 320 pixel axis of the CCD camera may be used for the spatial axis while the 240 pixel axis is used for the spectral axis. This means that 320 individual spectra can be acquired every 16.67 milliseconds.

In order for the camera 106 to measure light data from all parts/portions of the samples, the cuvettes 20 containing the samples are moved relative to the light measuring device 90 via the translation mechanism 70 of the sample carrier 12. In the illustrated embodiment, and as previously described, the cuvettes 20 and samples are supported by the stage 30 mounted on the translation mechanism 70 so that movement of the translation mechanism moves the stage 30 and samples. The translation mechanism 70 moves the samples through the field of view of the imaging assembly 14 at a generally constant velocity so that incrementally different parts/portions of each sample are illuminated by the line of light produced by the light source 88. This movement is synchronized with the operation of the imaging assembly 14 so that the light measuring device 90 acquires a spectral image at each of these incrementally different parts/portions. Each frame captured by the imaging assembly 14 is an adjacent, non-overlapping image along the line of light produced by the light source 88 illuminating the samples. Accordingly, a spectral image is acquired along each line of light for each part/portion of each sample on the stage 30 (i.e., spectral images of an entire sample may be acquired).

The speed at which the translation mechanism 70 moves the stage 30 (and the samples thereon) is generally determined by the width of the image line produced by the light source 88 and acquired by the light measuring device 90, and the readout speed of the light measuring device per image frame. The illustrated analysis system 10 may process about 1,000 samples in about 6.5 hours, or about two samples per minute. Generally, the total number of valid image lines is proportional to the total volume of the sample. In the illustrated embodiment, the start of the movement of the translation mechanism 70 may trigger image acquisition by the imaging assembly 14 (e.g., the light measuring device 90, etc.).

Figure 13:
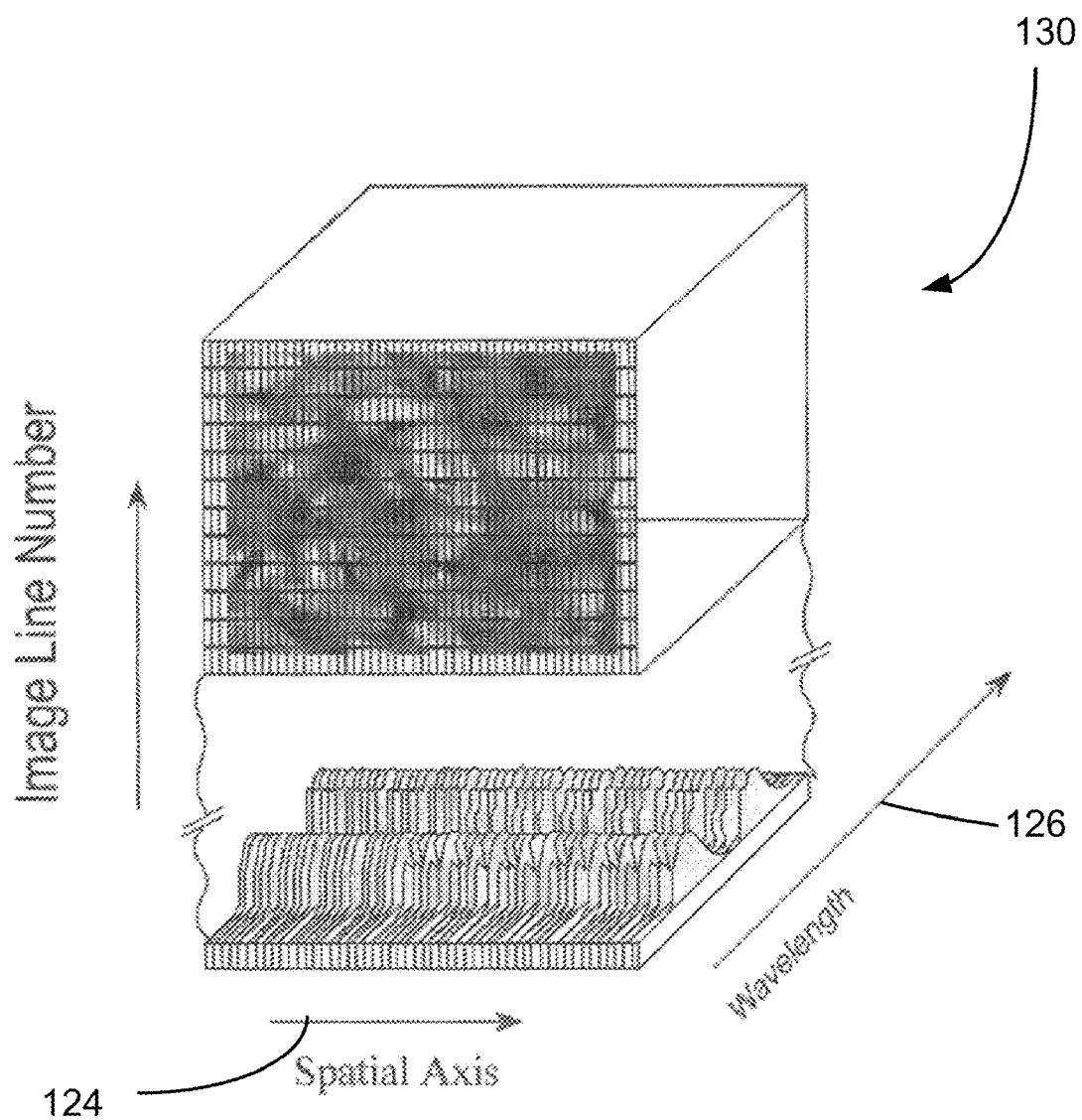
FIG. 13 is a perspective view schematically illustrating a hyperspectral datacube produced the automated system during analysis of a sample.
Figure 14:
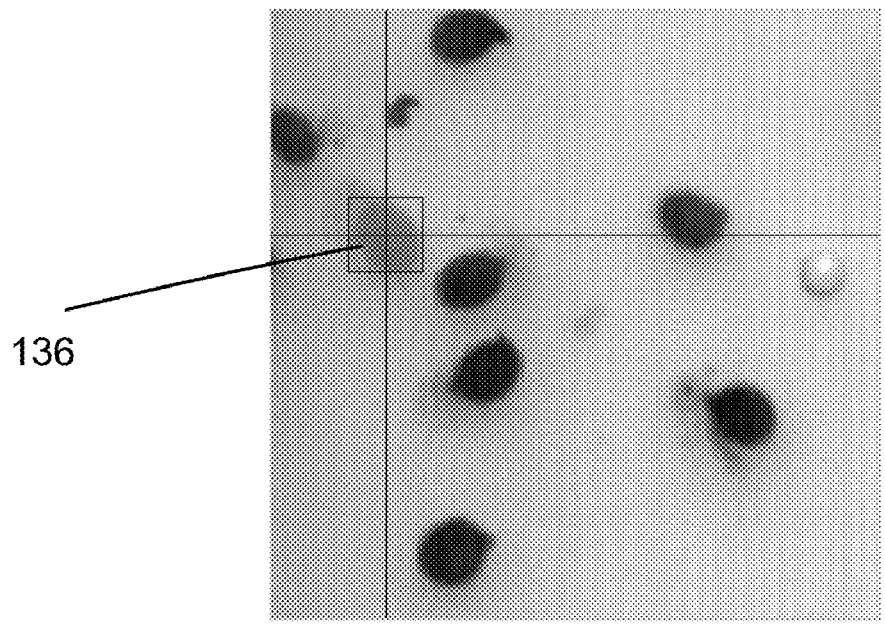
FIG. 14 is a digitized image of a known sample identifying a light colored soybean cyst nematode cyst.
Figure 15:
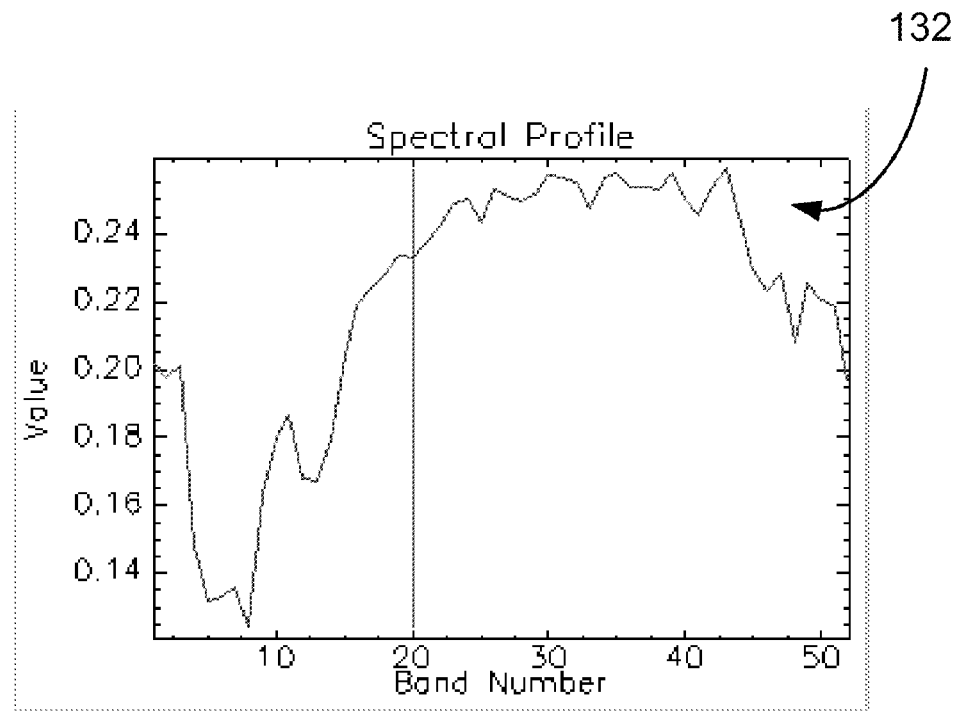
FIG. 15 is a graph of a spectral profile thereof.
Figure 16:
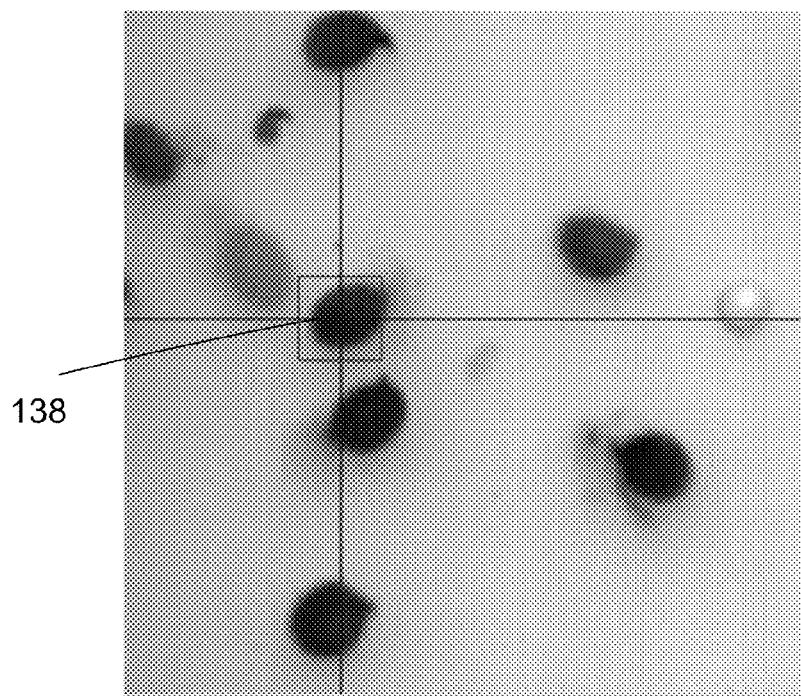
FIG. 16 is the digitized image of FIG. 14 identifying a dark colored soybean cyst nematode cyst.
Figure 17:
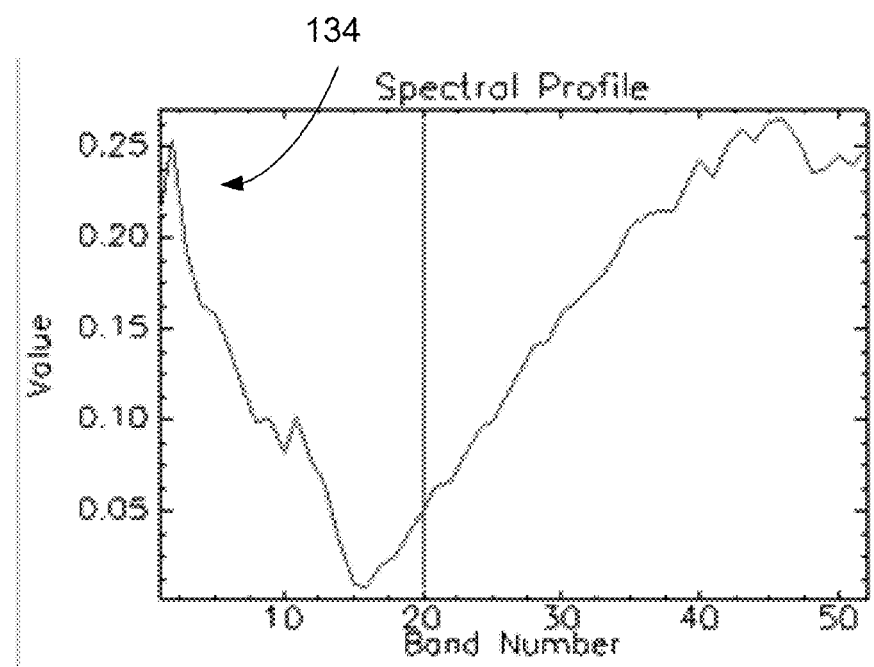
FIG. 17 is a graph of a spectral profile thereof.
Figure 18:
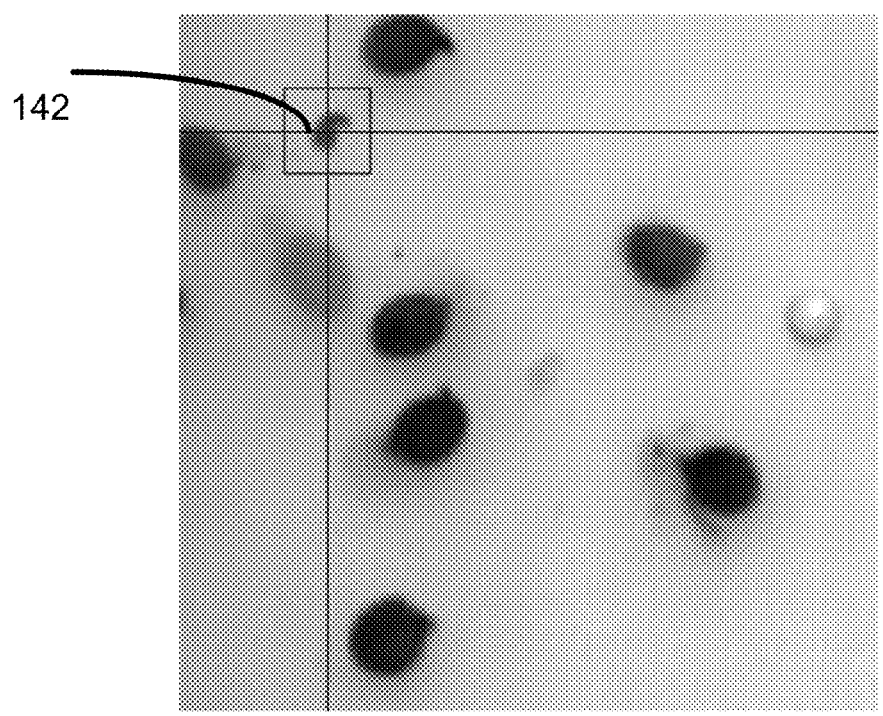
FIG. 18 is the digitized image of FIG. 14 identifying non-cyst debris in the sample.
Figure 19:
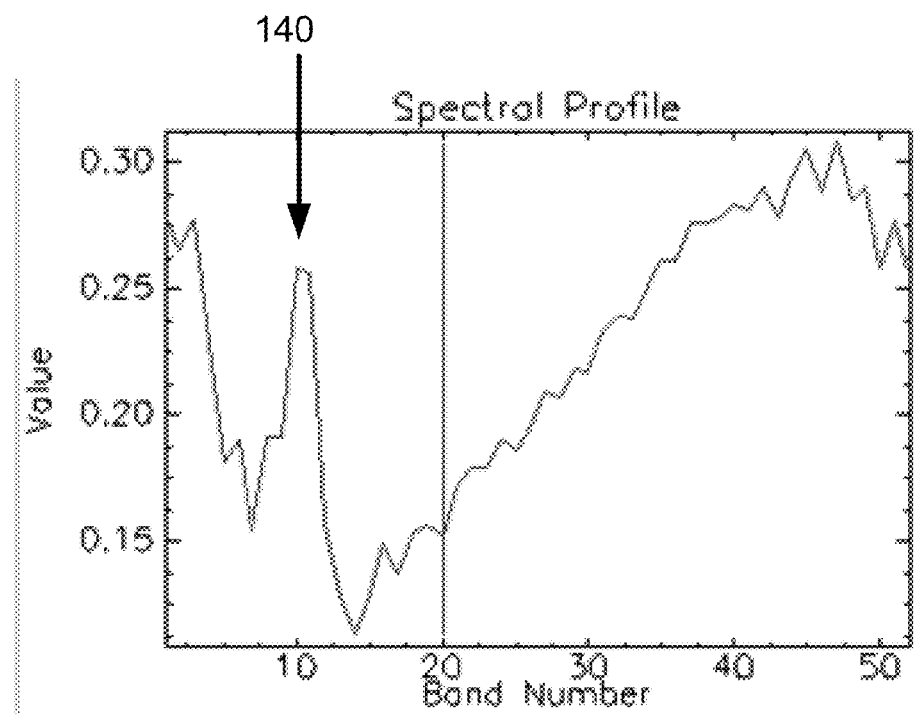
FIG. 19 is a graph of a spectral profile of the non-cyst debris.

As shown in FIG. 13, the spectral images acquired by the imaging assembly 14 for each sample may be combined to form a hyperspectral data cube digitized image (indicated at 130 in FIG. 13) for the sample. The data cube 130 is produced by appending adjacent image lines of the sample together. A gray-scale spectral image may be extracted from the hyperspectral data cube 130 by assigning unique wavelength planes to each of the red, green, and blue (R-G-B) color components.

The digitized images produced by the imaging assembly 14 can be comparatively processed against at least one model to determine whether pests are present in the analyzed samples. In the illustrated embodiment, the at least one model includes known spectral signatures for soybean cyst nematode cysts and non-cyst debris. The known spectral signatures may be measured, or determined, using control samples with known content. For example, FIGS. 14-19 illustrate a set of known spectral signatures for control samples with known content. The spectral signatures 132 and 134 in FIGS. 15 and 17, respectively, correspond to soybean cyst nematode cysts 136 and 138 respectively shown in FIGS. 14 and 16, and the spectral signature 140 in FIG. 19 corresponds to non-cyst debris 142 shown in FIG. 18. These known spectral signatures ultimately allow for discriminating soybean cyst nematode cysts from non-cyst material/debris.

Figure 20:
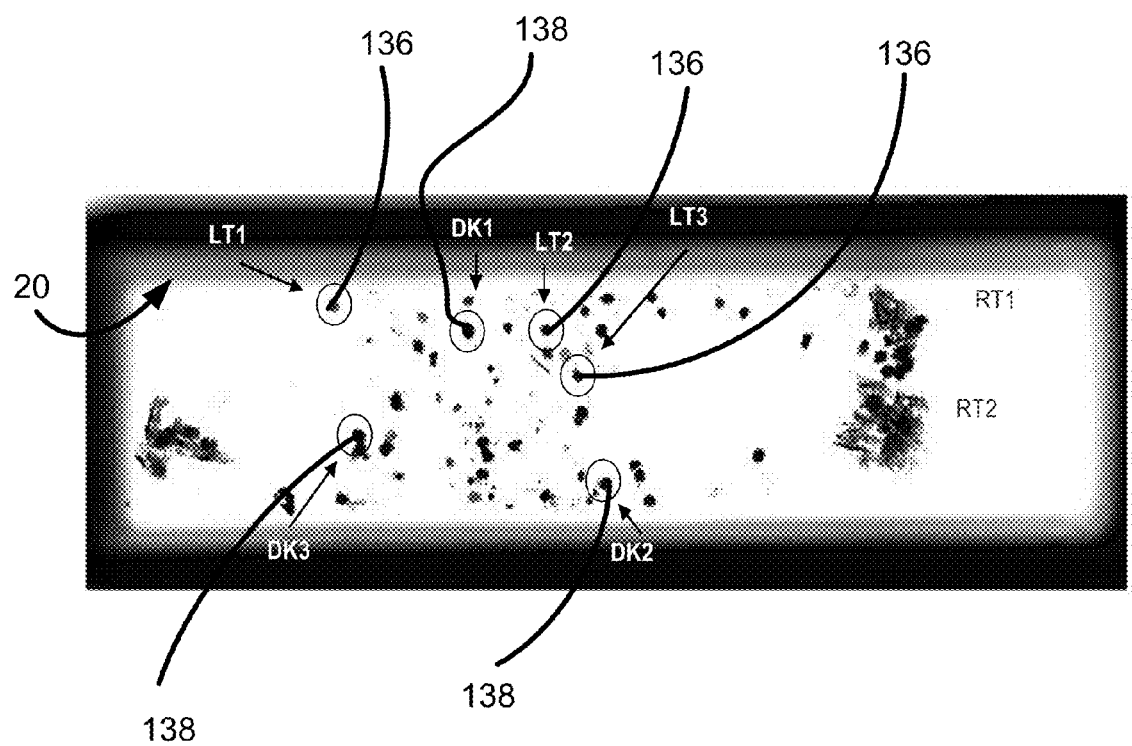
FIG. 20 is a digitized image of an example sample of soybean cyst nematode cysts taken from a soybean plant.

FIG. 20 illustrates an example digitized image of an agricultural sample in cuvette 20. Spectral information for each cluster in the sample may be compared to the known spectral signatures for soybean cyst nematode cysts and non-cyst debris, and a regression analysis (e.g., partial least squares discriminate analysis (PLS-DA), etc.) may be used to determine which clusters include cysts (136 and 138) and which do not (e.g., discriminate cysts from non-cysts). For example, a cyst may be identified in the agricultural sample by matching one or more component wavelength of the digitized image to one or more of the known cyst spectral signatures (i.e., determining what wavelengths in the image exhibit a substantially similar spectral profile to one of the known cyst spectral signatures). The location of the matching component wavelength(s) in the image corresponds to the location of the discrete special sample point(s) emitting the matching wavelength(s) in the sample, and thus identifies the location of the cyst in the sample. Once the entire digital image is analyzed, the number of confirmed/matched cysts in the image (and thus in the sample) can be tabulated and scored. Other algorithms may be used to process the samples, including, for example, thresholding via grey-line segmentation, morphological operations, principle component analysis, SIMCA (soft independent modeling of class analogy), edge detection, eroding detection, counting, classification routines such as K-means, etc. In addition, image analysis programs may be used to implement the algorithms for analysis. For example, programs from ENVI from Research Systems, Matlab from Mathworks, etc. may be used.

Figure 21:
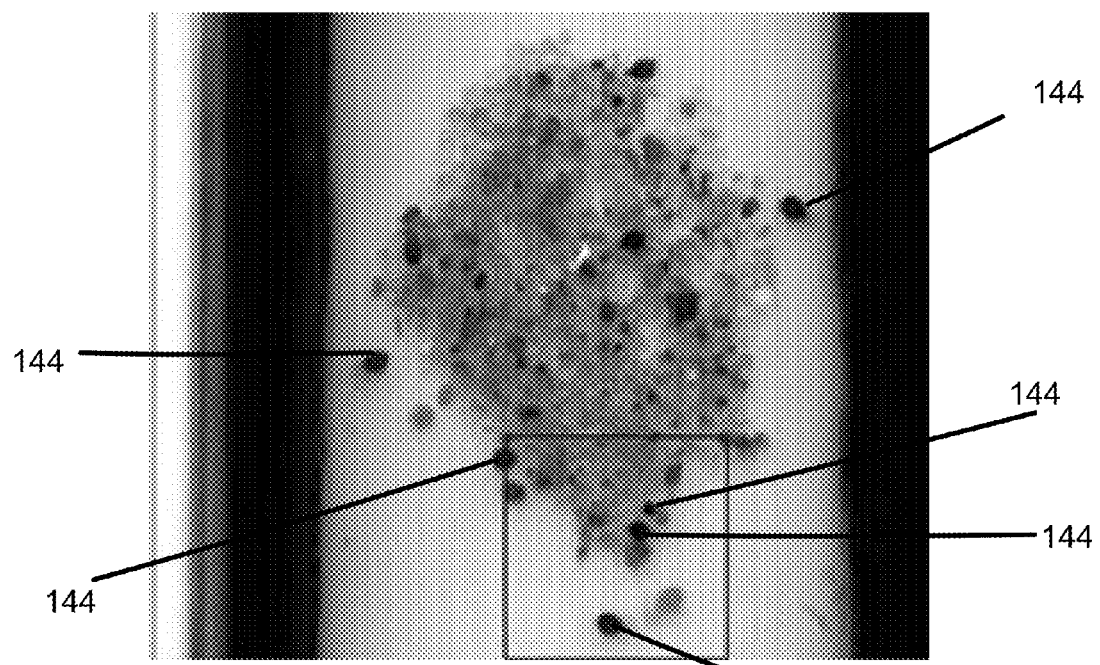
FIG. 21 is a digitized image of another example sample comprising soybean cyst nematode cysts taken from a soybean plant.
Figure 22:
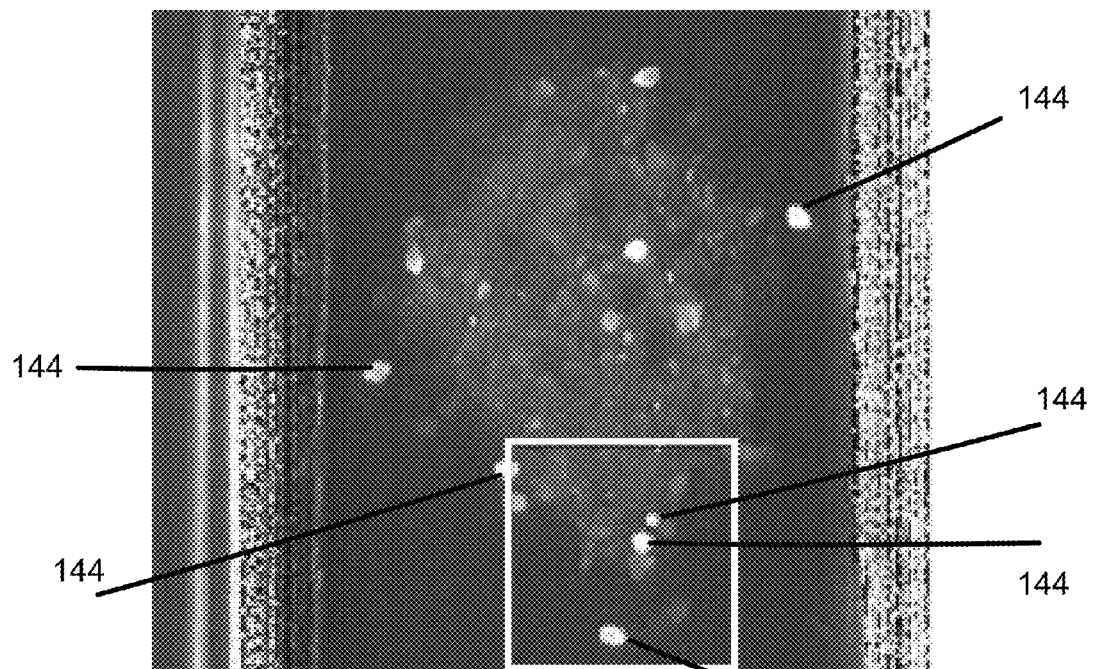
FIG. 22 is the digitized image of FIG. 21 with background removed and cysts lightened.

As shown in FIGS. 21 and 22, thresholding, filtering, and PLS-DA may be used to remove unwanted background from digitized images of samples while also lighting up soybean cyst nematode cysts (indicated at 144). This may further discriminate cysts from other material in the sample and may improve cyst identification as well as cyst quantification in each sample.

In other example embodiments, analysis systems and/or methods may include any combination of one or more features, components, processes, etc. disclosed herein.

In other example embodiments, a system may include a data processor (e.g., a computer, etc.) for collecting digitized images of samples. The data processor may be programmed to process the samples against one or more models to identify and/or quantify pests in a sample. In addition, the data processor may control operation of components of the system, including, for example, collection of image frame data from a light measuring device, movement of samples by a sample carrier, etc.

In still other example embodiments, a system for analyzing agricultural products may be used in combination with a breeding methodology to select plants that exhibit a resistance to pests (e.g., soybean cyst nematode cysts). Plants that are analyzed may receive a score corresponding to the number of pests present in the sample. A plant may exhibit a desired trait if the score is, for example, below a minimum value.

FIGS. 23-30 illustrate example components of an example embodiment of a processing assembly including one or more aspects of the present disclosure. The illustrated processing assembly is substantially automated. The processing assembly could be used, for example, with the analysis system 10 previously described and illustrated herein (e.g., in connection with FIGS. 1-22, etc.). The processing assembly is operable, for example, to separate pests from plants to produce a sample (e.g., an agricultural sample, etc.) suitable for analysis using the analysis system 10, etc. The analysis may include, for example, imaging analysis to quantify pest infestation in the plants, analysis to evaluate susceptibility of the plants to infestation, etc. Any agricultural products (e.g., plants, etc.) and/or samples (e.g., agricultural samples, etc.) and/or pests, infestations, pathogen infections, other botanical conditions or characteristics, etc. suitable for use with the analysis system 10 may also be used with the illustrated processing assembly.

Figure 28:
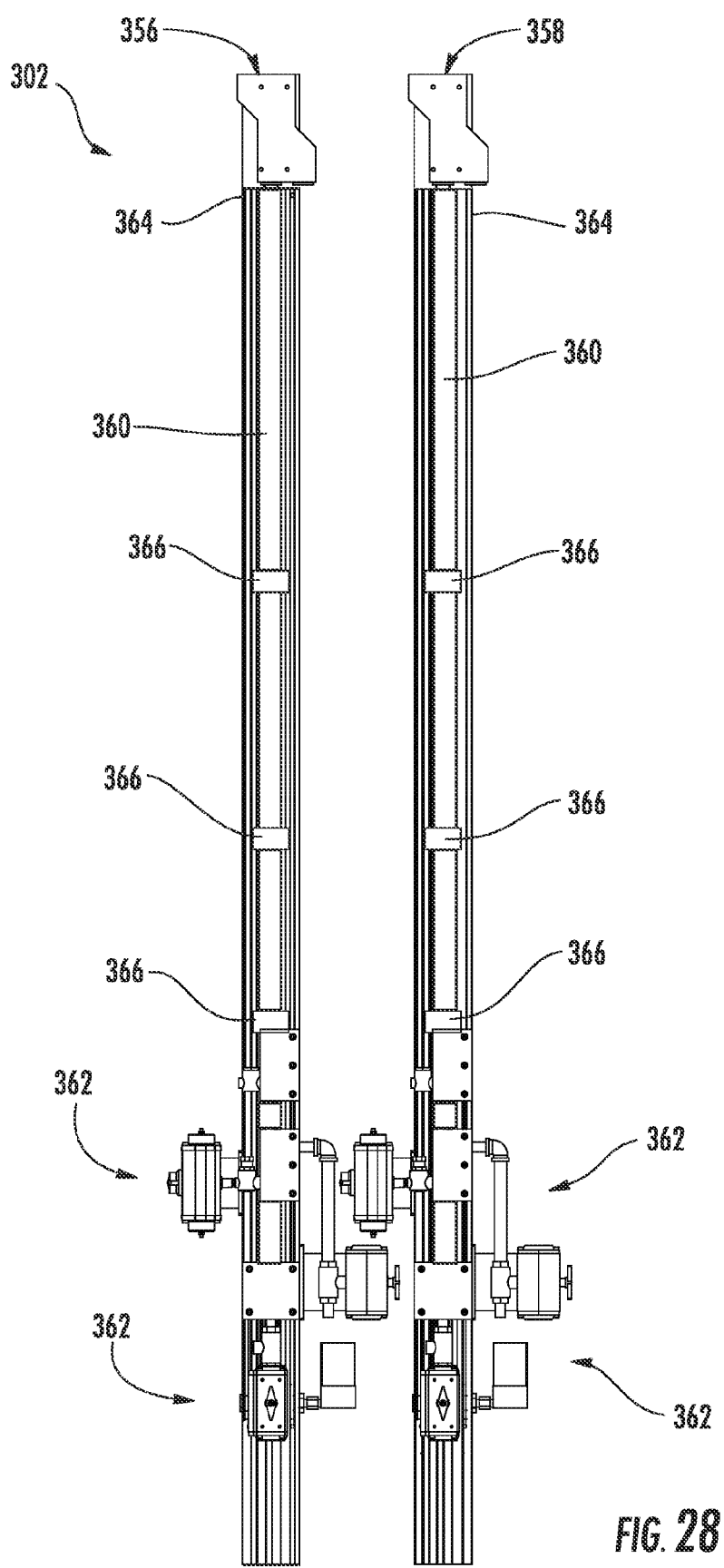
FIG. 28 is a front elevation view of the elutriation unit of FIG. 27.
Figure 29:
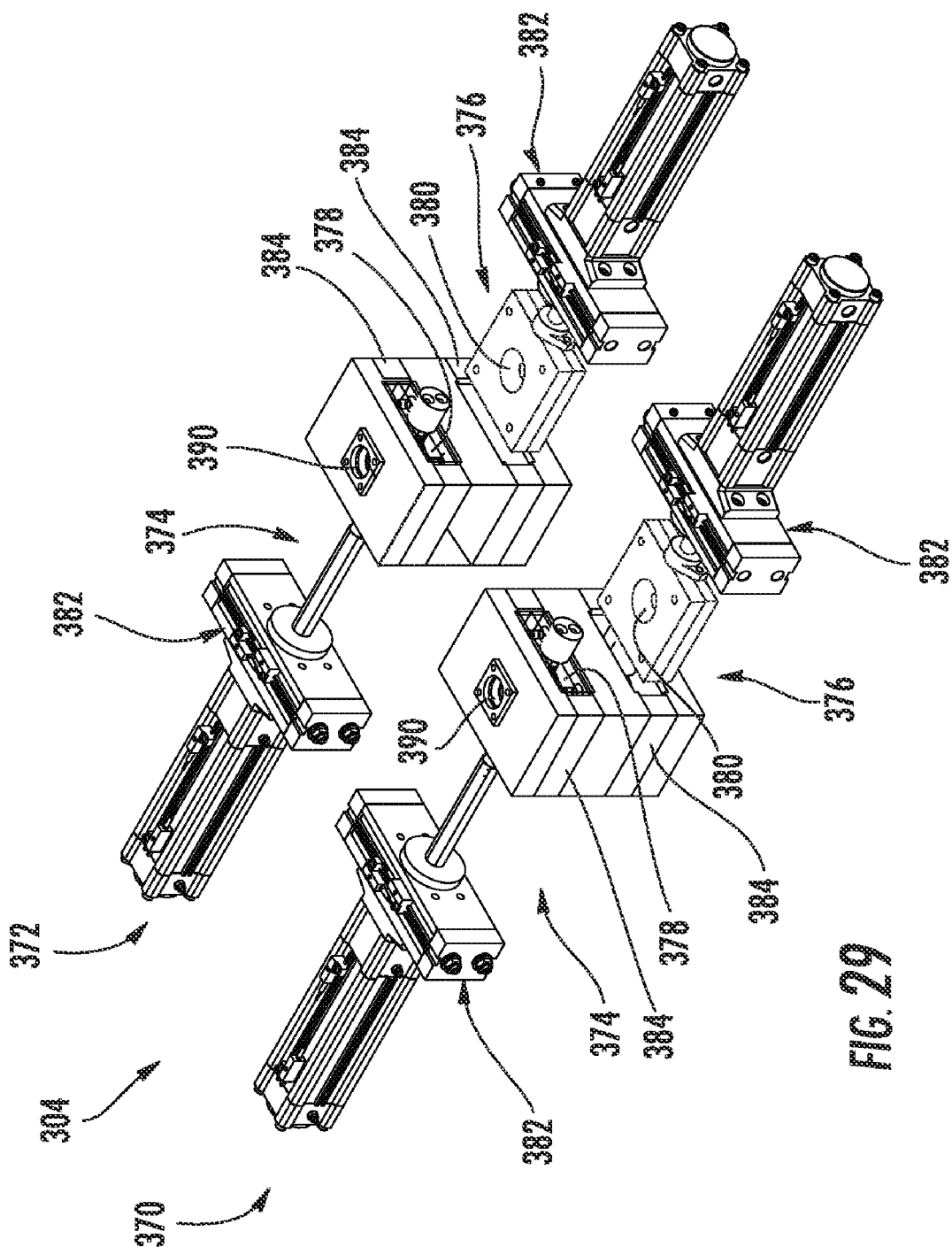
FIG. 29 is a perspective view of an example embodiment of a collection unit including one or more aspects of the present disclosure and operable as part of the processing assembly together with the sieving tower of FIG. 23, the transfer unit of FIG. 25, and the elutriation unit of FIG. 27.
Figure 30:
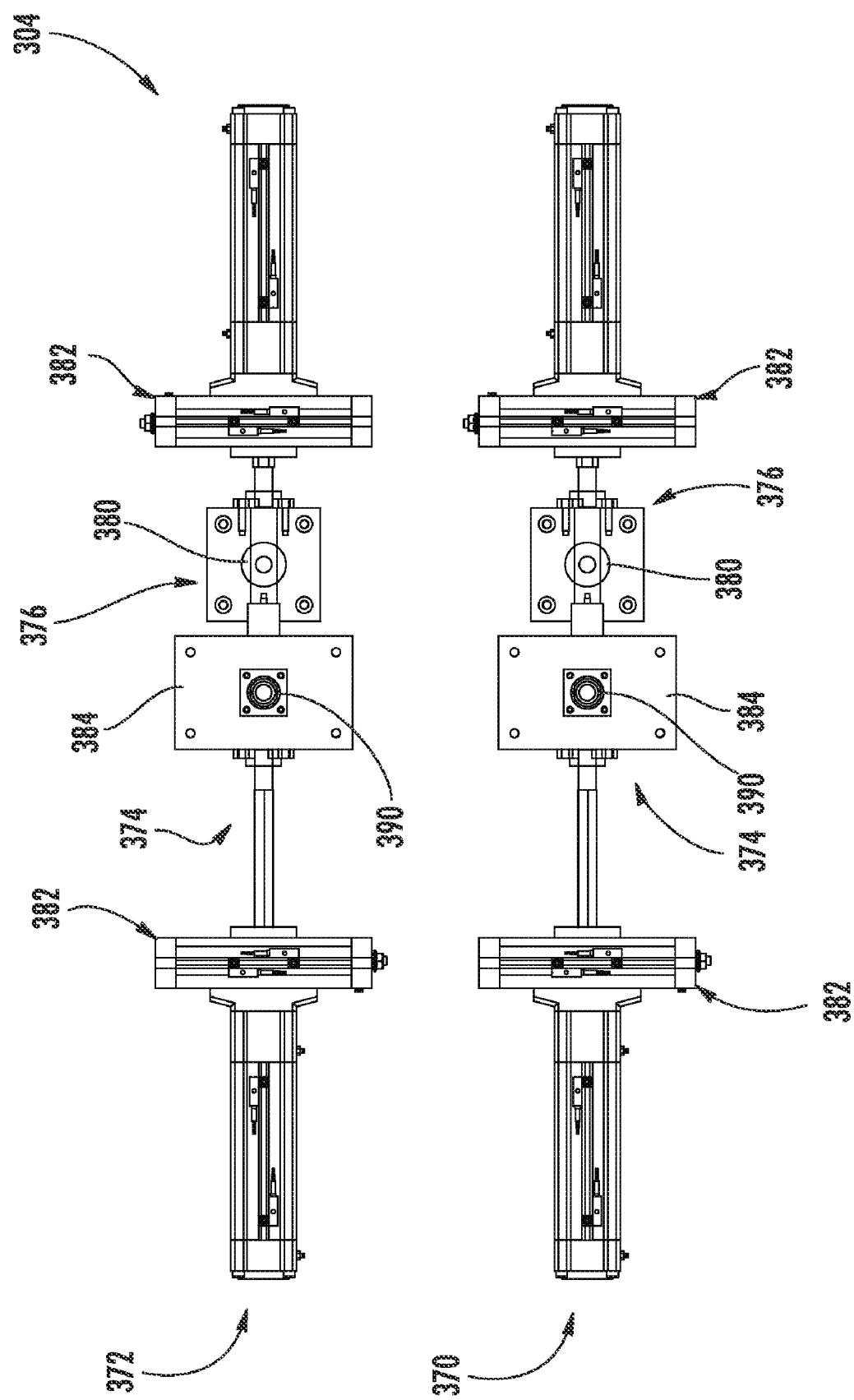
FIG. 30 is a front elevation view of the collection unit of FIG. 29.

The illustrated processing assembly generally includes a sieving tower 300 (e.g., FIGS. 23 and 24, etc.), an elutriation unit 302 (e.g., FIGS. 27 and 28, etc.), and a collection unit 304 (e.g., FIGS. 29 and 30, etc.). The sieving tower 300 and/or the elutriation unit 302 and/or the collection unit 304 may be broadly referred to as a separating unit (each individually or collectively in any combination).

Briefly, plant materials (e.g., plants including planting media, pests, etc.) can be introduced (manually, automatically, combinations thereof, etc.) into the sieving tower 300 to initially separate different parts of the plant materials (e.g., to separate planting media and pests from the plants (e.g., from roots of the plants, etc.), etc.). Separated parts (e.g., the planting media and pests separated from the plants, etc.) of the plant materials can then be transferred to the elutriation unit 302 for further separation (e.g., for separating pests from the planting media, etc.). The further separated parts (e.g., the separated pests, etc.) can then be deposited (e.g., via the collection unit 304, etc.) into a receptacle (e.g., cuvette 20, cuvette 220, etc.) to create a sample for subsequent analysis (e.g., by the analysis system 10, etc.).

Figure 23:
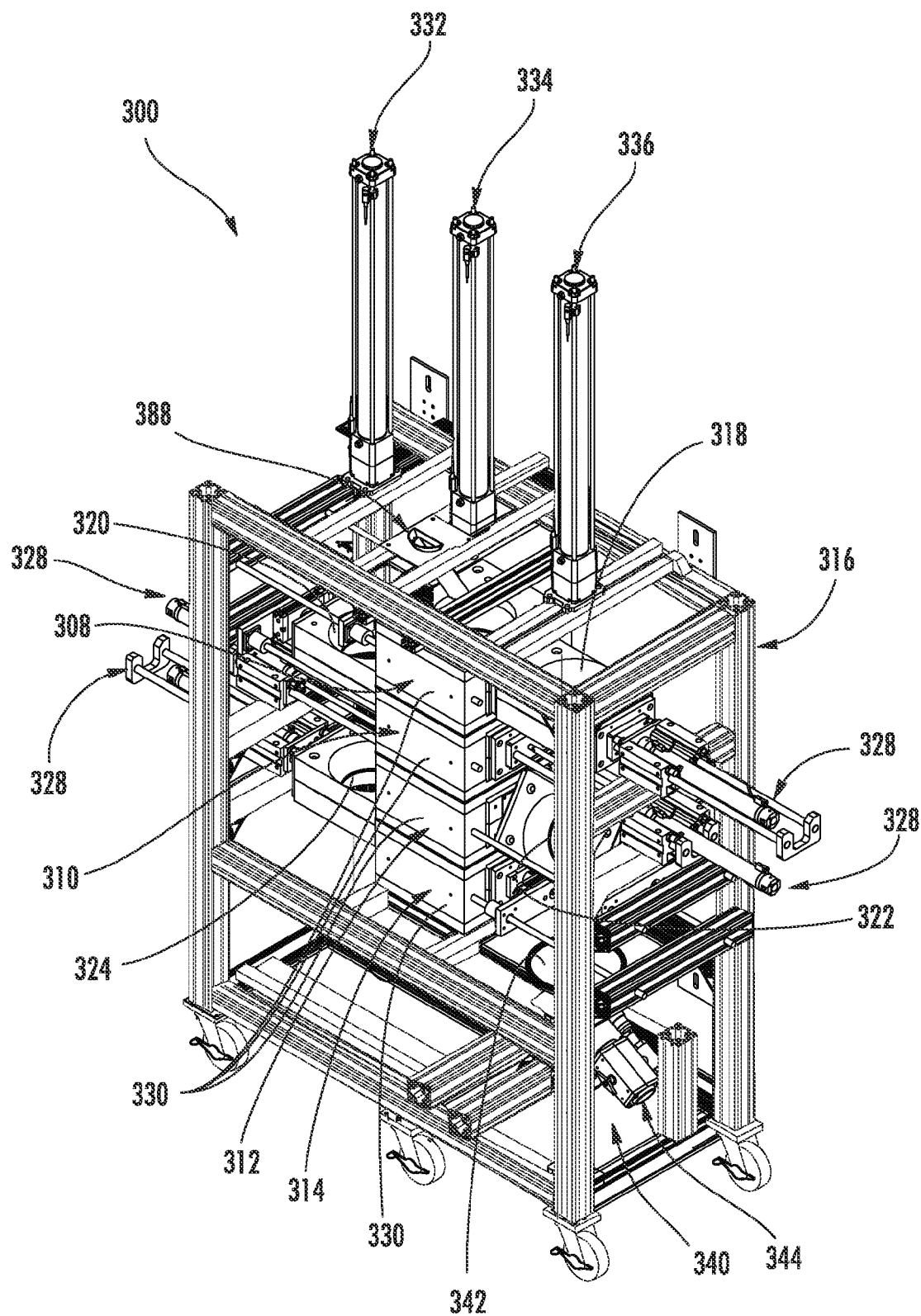
FIG. 23 is a perspective view of an example embodiment of a sieving tower including one or more aspects of the present disclosure and operable as part of a processing assembly to separate plant materials.
Figure 24:
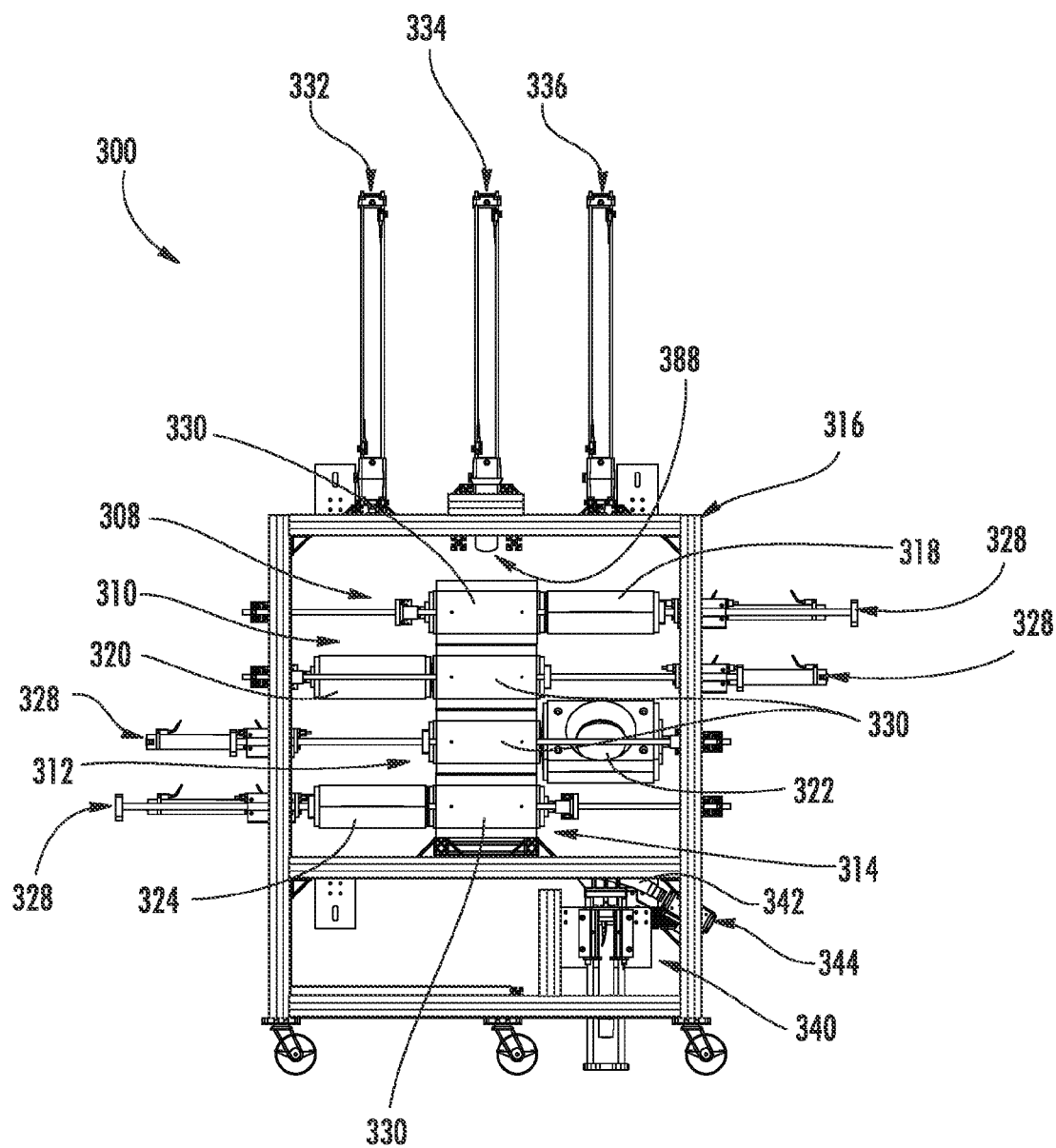
FIG. 24 is a front elevation view of the sieving tower of FIG. 23.

As shown in FIGS. 23 and 24, the sieving tower 300 generally includes four vertically stacked sieves 308, 310, 312, and 314 supported by a frame 316. The sieves 308, 310, 312, and 314 are operable to at least partially separate (e.g., sieve, filter, etc.), based on size, different plant materials (e.g., plants, leaves, roots, planting media, pests, etc.). The illustrated sieves 308, 310, 312, and 314 include screens 318, 320, 322, and 324 that are differently sized and that progressively decrease in size from a first sieve 308 (located toward an upper portion of the frame 316) to a fourth sieve 314 (located toward a lower portion of the frame 316). Intermediate sized second and third sieves 310 and 312 are generally stacked between the first and fourth sieves 308 and 314. The sieves 308, 310, 312, and 314 (and their screens 318, 320, 322, and 324) operate to retain (depending on size) separated plant materials in the sieving tower 300 as desired for further processing (e.g., waste, treatment, recycle, analysis, etc.).

In the illustrated embodiment, for example, the first, second, third, and fourth sieves 308, 310, 312, and 314 respectively include a 12 mesh screen 318, a 30 mesh screen 320, a 40 mesh screen 322, and a 50 mesh screen 324 for separating operation. In other example embodiments, processing assemblies may include more than or less than four sieves and/or screens. In still other example embodiments, processing assemblies may include one or more sieves and/or screens that have one or more different screen sizes than disclosed herein (e.g., a sieve having a screen with a 60 mesh size, etc.).

The illustrated sieves 308, 310, 312, and 314 each include an actuator 328 and a housing 330. The actuators 328 are operable to move (e.g., extend, slide, etc.) the screens 318, 320, 322, and 324 longitudinally into and out of the respective housings 330, as desired. The actuators 328 are also operable to rotate extended screens 318, 320, 322, and 324 to position them for removing separated plant materials retained thereon for further processing. For example, the screens 318, 320, 322, and 324 can be moved longitudinally out of their respective housings 330 to either a first extended position (e.g., toward the left of their housings 330 in FIG. 24, etc.) or a second extended position (e.g., toward the right of their housings 330 in FIG. 24, etc.). In FIG. 24, for example, the third screen 322 is shown moved longitudinally out of its housing 330 to the second extended position (e.g., toward the right of its housing 330, etc.), and partially rotated.

Fluid jets 332, 334, and 336 are supported (e.g., coupled to the frame 316 by suitable means, etc.) generally above the sieves 308, 310, 312, and 314 for use in spraying fluid (e.g., any suitable fluids, etc.) through the sieves 308, 310, 312, and 314 (e.g., through the screens 318, 320, 322, and 324 of the respective sieves 308, 310, 312, and 314, etc.) as desired. The fluids may be pressurized fluids. For example, a first fluid jet 332 is operable to spray fluid (e.g., water, other suitable fluid, etc. etc.) through one or more of the screens 318, 320, 322, and 324 when they are moved to the first extended position for helping remove (e.g., rinse, flush, etc.) separated materials retained on the screens 318, 320, 322, and 324 when in this position (as will be described in more detail hereinafter). A second fluid jet 334 is operable to spray fluid through the sieve screens 318, 320, 322, and 324 when positioned in their housings 330. This fluid helps move (e.g., rinse, flush, etc.) plant materials (e.g., plants, planting media materials, pests, etc.) desired to be separated through the sieves 308, 310, 312, and 314 and their screens 318, 320, 322, and 324. A third fluid jet 336 is operable to spray fluid through the screens 318, 320, 322, and 324 when they are moved to the second extended position and rotated for helping remove separated materials retained on the screens 318, 320, 322, and 324 when in this position (as will be described in more detail hereinafter).

With continued reference to FIGS. 23 and 24, the sieving tower 300 also includes a transfer unit 340 supported by the frame 316 generally below the sieves 308, 310, 312, and 314. The transfer unit 340 operates to receive, collect, etc. separated plant materials removed from select ones of the screens 318, 320, 322, and 324 (e.g., from the third and fourth screens 322 and 324 in the illustrated embodiment, as will be described in further detail hereinafter, etc.) when moved to the second extended position and rotated. The transfer unit 340 also receives the fluid sprayed from the third jet 336 used to remove the plant materials from the select ones of screens 318, 320, 322, and 324 moved to the second extended position. The transfer unit 340 further operates to transfer the received plant materials to the elutriation unit 302 for further processing.

Figure 25:
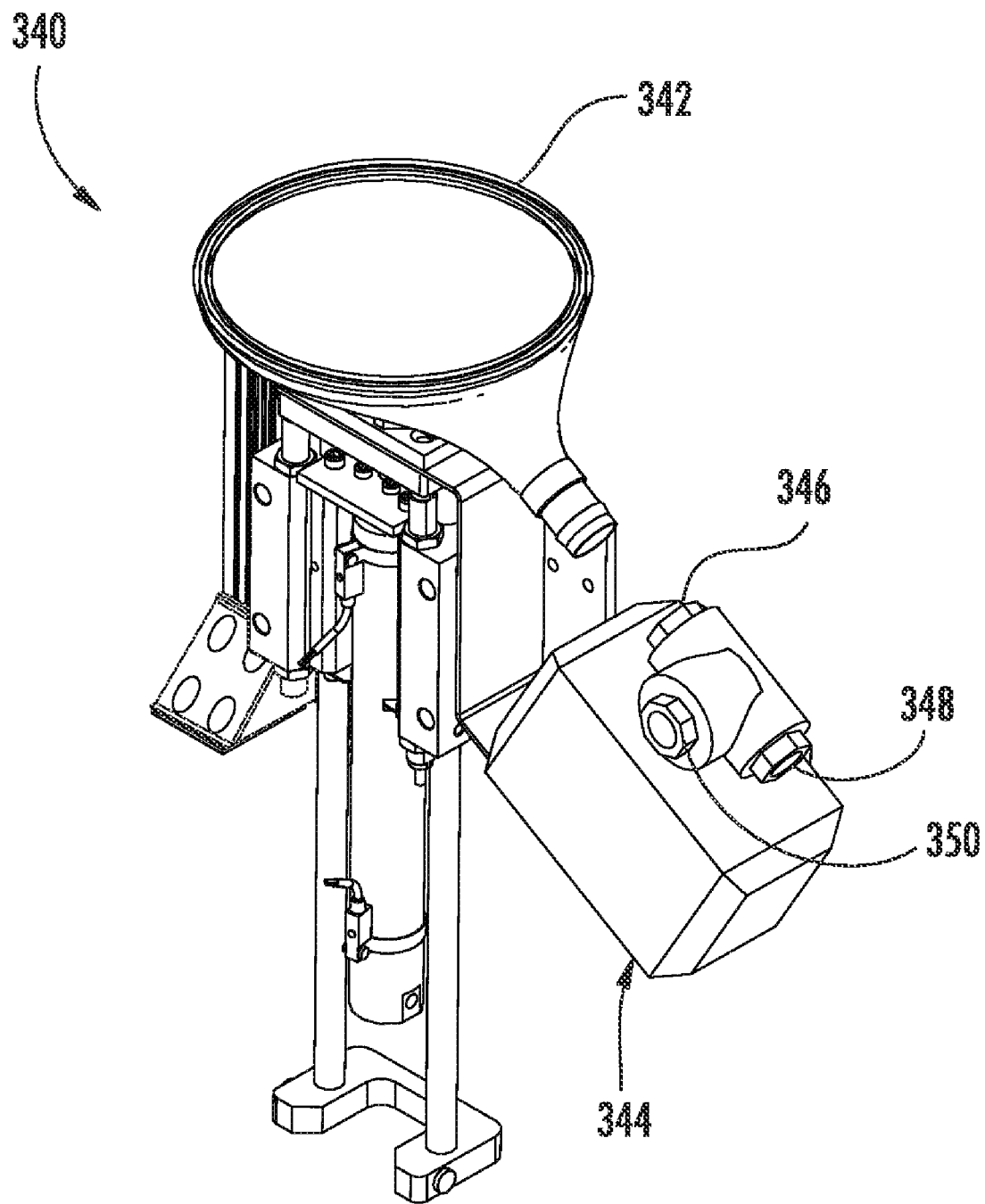
FIG. 25 is a perspective view of an example embodiment of a transfer unit including one or more aspects of the present disclosure and operable as part of the processing assembly together with the sieving tower of FIG. 23.
Figure 26:
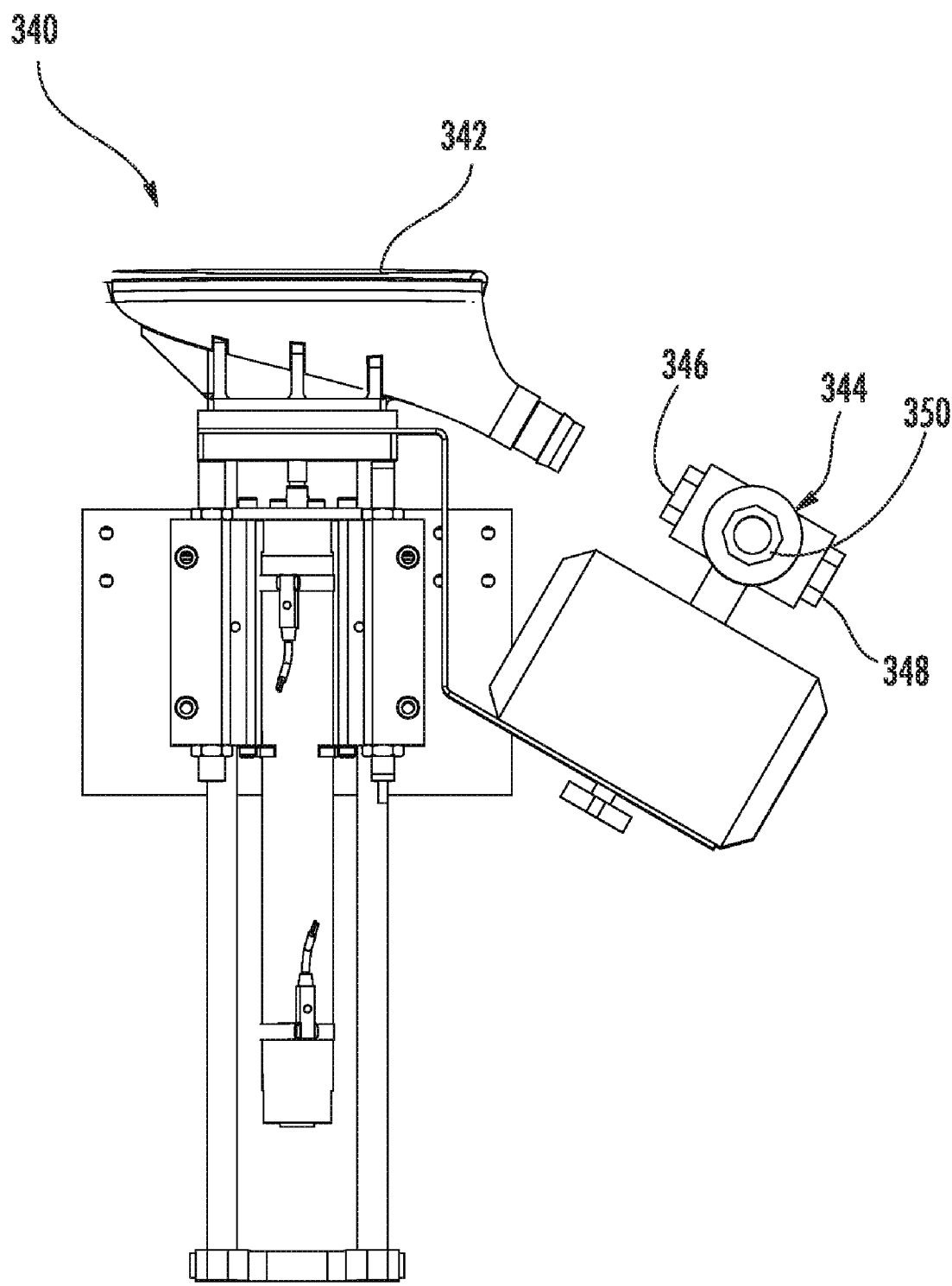
FIG. 26 is a front elevation view of the transfer unit of FIG. 25.
Figure 27:
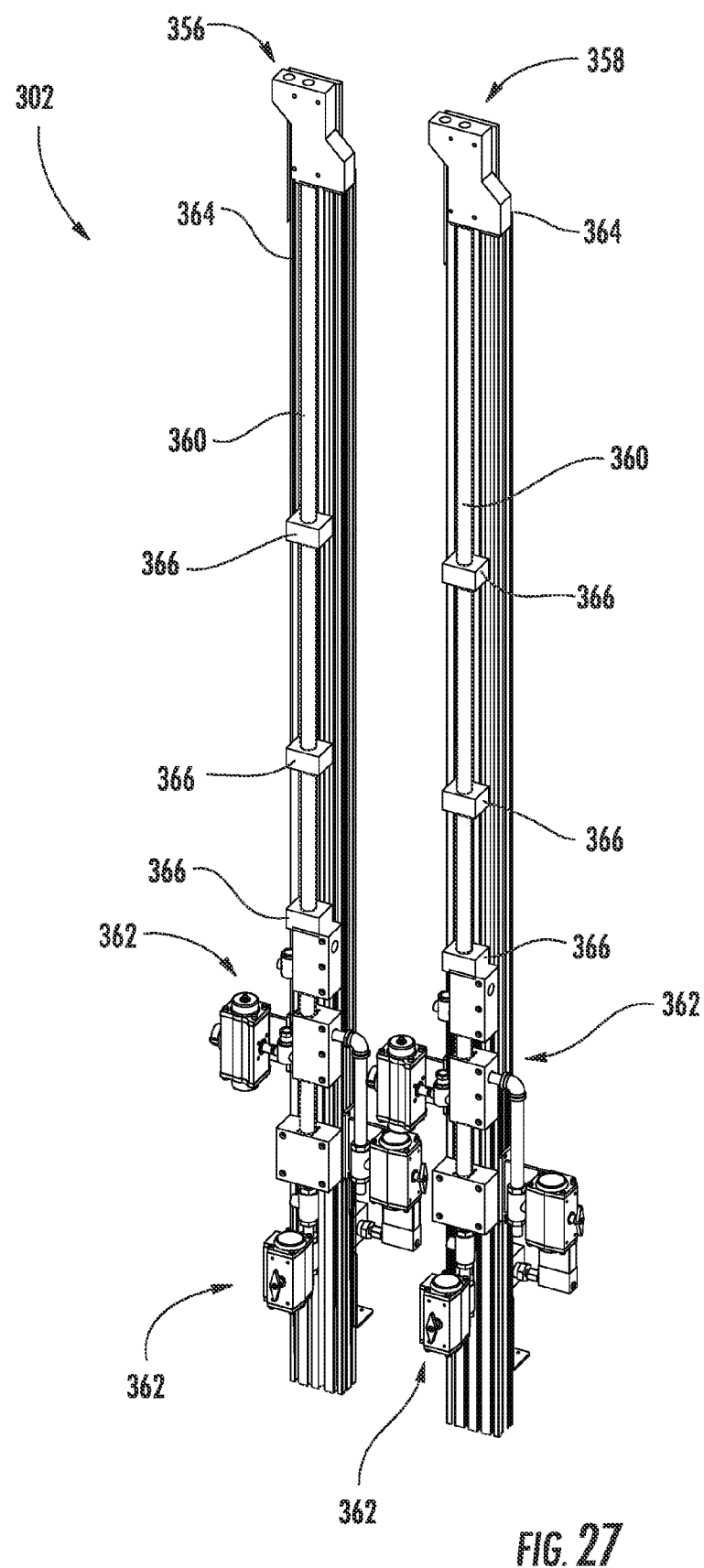
FIG. 27 is a perspective view of an example embodiment of an elutriation unit including one or more aspects of the present disclosure and operable as part of the processing assembly together with the sieving tower of FIG. 23 and the transfer unit of FIG. 25.

With additional reference to FIGS. 25 and 26, the illustrated transfer unit 340 includes a funnel 342 configured to receive the separated materials removed from the select ones of screens 318, 320, 322, and 324 moved to the second extended position. And a valve structure 344 having an intake 346 and first and second discharges 348 and 350 is configured to selectively direct the received plant materials to a select one of first and second elutriation towers 356 and 358 (FIGS. 28 and 29) of the elutriation unit 302. Suitable conduit (not shown) can couple the funnel 342 to the valve structure 344, and suitable conduit (not shown) can couple the valve structure 344 to the elutriation towers 356 and 358. More specifically, suitable conduit can couple the funnel 342 to the intake 346 of the valve structure 344, and suitable conduit can couple the first and second discharges 348 and 350 of the valve structure 344, respectively, to the first and second elutriation towers 356 and 358. The valve structure 344 can be actuated (e.g., manually, automatically, etc.) to either direct plant materials to the first elutriation tower 356 (e.g., via the first discharge 348, etc.) or to the second elutriation tower 358 (e.g., via the second discharge 350, etc.) as desired. Suitable pumps (not shown) can also be used to transfer, move, etc. the materials from the transfer unit 340 to the elutriation towers 356 and 358. And check vales (not shown) may be included between the transfer unit 340 and the pumps and/or between the pumps and the elutriation towers 356 and 358 as desired.

Intermediate sieves (not shown) may also be included inline between the valve structure 344 of the transfer unit 340 and each of the elutriation towers 356 and 358. These intermediate sieves may operate to separate the fluid sprayed from the third jet 336 (e.g., the fluid used to remove the separated plant materials from the select ones of the screens 318, 320, 322, and 324 moved to the second extended position, etc.) from the plant materials being transferred to the elutriation towers 356 and 358. Fresh fluid may then be introduced (e.g., pumped, etc.) through the intermediate sieves to remove the materials retained therein and transfer the materials to the elutriation towers 356 and 358. The intermediate sieves may include screens having any suitable size, for example, an 80 mesh size, etc. within the scope of the present disclosure.

With reference now to FIGS. 28 and 29, the first and second elutriation towers 356 and 358 of the illustrated elutriation unit 302 are shown. Suitable structure may be provided to support the elutriation unit 302 (and the two elutriation towers 256 and 258) as necessary adjacent the sieving tower 300. For example, the structure may include a frame that couples the elutriation unit 302 to the frame 316 of the sieving tower 300, etc.

The elutriation towers 356 and 358 operate to receive the separated plant materials removed from the select ones of the screens 318, 320, 322, and 324 moved to the second extended position (e.g., the third and fourth screens 322 and 324 in the illustrated embodiment, etc.), via the transfer unit 340 and intermediate sieves, and to separate lighter portions of the plant materials (e.g., pests, etc.) from heavier portions of the plant materials (e.g., planting media, etc.). This separating (e.g., elutriation, etc.) operation will be described in more detail hereinafter.

The elutriation towers 356 and 358 are generally tall, elongate, and vertically oriented structures. Each of the elutriation towers 356 and 358 includes an elongate tube 360 for elutriating the received plant materials, and sensors 362 adjacent the tube 360 for monitoring fluid flow through the tube 360 and for monitoring plant material build up in the tube 360 (e.g., deposited plant materials as a byproduct of the elutriation operation, etc.). In the illustrated embodiment, the tube 360 is mounted to a support frame 364 (e.g., via brackets 366, etc.), and the sensors 362 are mounted generally around the tube 360 by suitable means. Elutriation towers may have different configurations than disclosed herein within the scope of the present disclosure. For example, elutriation towers may include differently sized tubes, etc.

Figure 31:
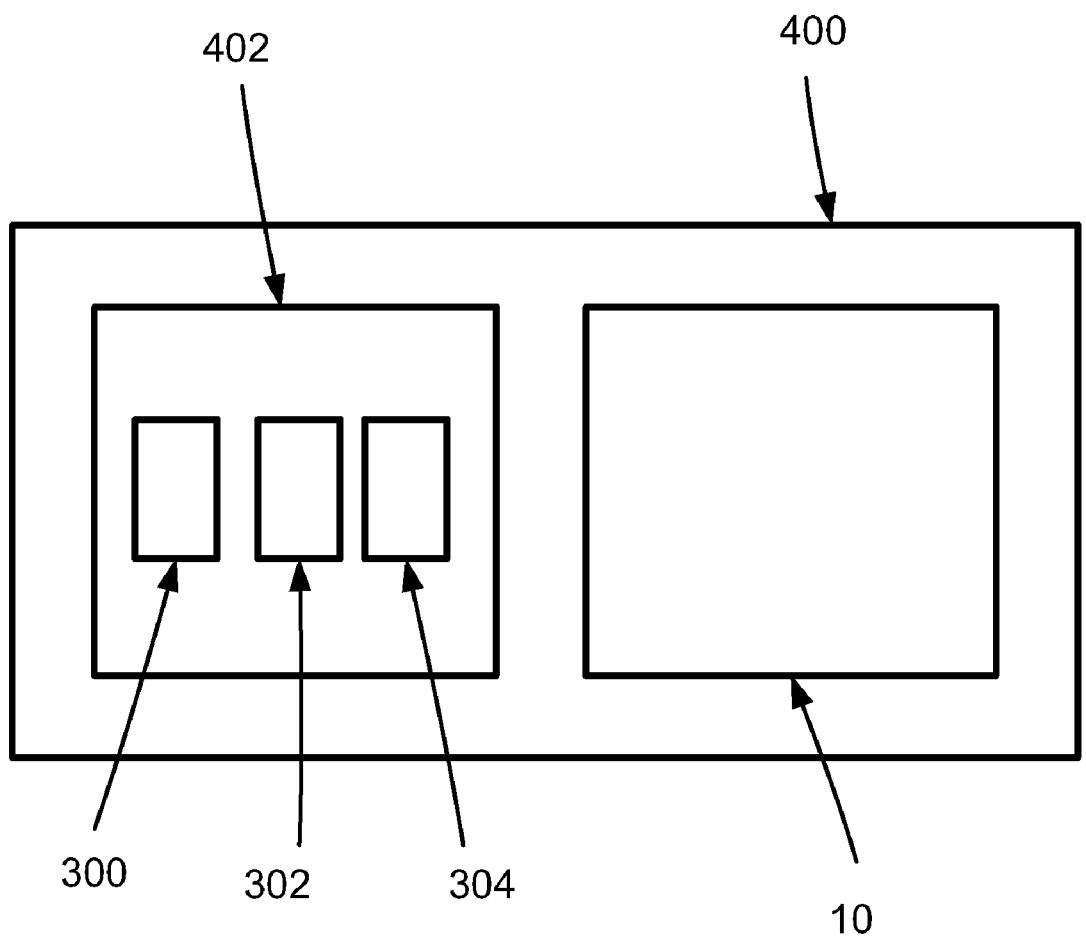
FIG. 31 is a block diagram of an example apparatus including one or more aspects of the present disclosure operable to evaluate a plant for presence of pests, and including the example components of the processing assembly of FIGS. 23-30 and the example analysis system of FIG. 1.

FIGS. 30 and 31 show the example collection unit 304, which is operable to receive the separated lighter portions of plant materials from the elutriation towers 356 and 358 for sample preparation. Suitable structure may be provided to support the collection unit 304 as necessary adjacent the sieving tower 300 and/or elutriation unit 302 (and elutriation towers 256 and 258). For example, the structure may include a frame that couples the collection unit 304 to the frame 316 of the sieving tower 300 and/or to the frame of the elutriation unit 302, etc.

The illustrated collection unit 304 includes first and second subunits 370 and 372, each including two stacked sieves 374 and 376 with respective screens 378 and 380. A first upper sieve 374 of each subunit 370 and 372 includes a larger screen 378, and a second lower sieve 376 of each subunit 370 and 372 includes a smaller screen 380. For example, in the illustrated embodiment, the upper sieve 374 of each subunit 370 and 372 includes a 30 mesh screen 378, and the lower sieve 376 of each subunit 370 and 372 includes a 60 mesh screen 380. The larger screens 378 of the upper sieves 374 operate to retain any larger portions of plant materials that may be received from the elutriation towers 356 and 358. The smaller screens 380 of the lower sieves 376 operate to retain smaller portions of plant materials that pass through the larger screens 378 and that are to be subsequently dispensed into receptacles to form samples for analysis.

The illustrated sieves 374 and 376 of the first and second subunits 370 and 372 also include actuators 382 operable to move (e.g., extend, slide, etc.) the respective screens 378 and 380 longitudinally into and out of respective housings 384, as desired. The actuators 382 are also operable to rotate the extended screens 378 and 380 to position them for removing plant materials retained thereon for further processing. For example, the screens 378 of the upper sieves 374 of the illustrated subunits 370 and 372 can be moved longitudinally out of their respective housings 384 to a first extended position (e.g., toward the left of their housings 384 in FIG. 30, etc.). And the screens 380 of the lower sieves 376 of the illustrated subunits 370 and 372 can be moved longitudinally out of their respective housings 384 to a second extended position (e.g., toward the right of their housings 384 in FIG. 30, etc.).

Fluid jets (not visible) can be positioned generally above the sieves 374 and 376 for each subunit 370 and 372 for use in spraying fluid through the sieves 374 and 376 (e.g., through the screens 378 and 380 of the sieves 374 and 376, etc.) as desired. For example, fluid jets may be operable to spray fluid through sieve screens 378 when they are moved to the first extended position and rotated for helping remove plant materials retained on the screens 378 when in this position (as will be described in more detail hereinafter). Other fluid jets (not visible) may be operable to spray fluid through sieve screens 380 when they are moved to the second extended position and rotated for helping remove plant materials retained on the screens 380 when in this position (as will be described in more detail hereinafter).

General operation of the processing assembly will now be described for separating different parts of plant materials (e.g., separating pests from a plant to produce a sample of pests for analysis, etc.). For example, plants suitable for use with the illustrated processing assembly may be grown from seeds under generally controlled conditions, for example in a greenhouse. And following germination, the example plants may be inoculated with desired pests for subsequent analysis. The infected plants may be cultivated for about thirty days following inoculation and then harvested. The harvested plants (including planting media, pests, etc. provided therewith) can then be introduced (manually, automatically by an automated system, assembly, apparatus, etc., combinations thereof, etc.) into the processing assembly for operation to separate, for example, the pests from the plants and planting media (e.g., in preparation for further analysis of a prepared sample, for example, by the analysis system 10, etc.).

To initiate operation, the screens 318, 320, 322, and 324 of the sieves 308, 310, 312, and 314 (of the sieving tower 300) are initially positioned within their respective housings 330 (e.g., in a sieving position, etc.). And plant materials (e.g., a harvested plant including its planting media, pests, etc.) are introduced into the sieving tower 300 for initial separating operation. The plant materials can be introduced through an upper chute 388 of the sieving tower 300 generally above the stacked housings 330. The plants fall through the upper chute 388, and selectively move into (and through, depending on their sizes) the screens 318, 320, 322, and 324 of the sieves 308, 310, 312, and 314. For example, in the illustrated embodiment, the first and second sieves 308 and 310 operate to retain larger plant materials such as roots and larger planting media materials for removal. And the third and fourth sieves 312 and 314 operate to retain smaller plant materials such as pests and smaller size planting media materials for further processing.

As the plant materials are being introduced into the sieving tower 300, fluid from the second fluid jet 334 is sprayed through the sieve screens 318, 320, 322, and 324 to help rinse the plant materials (e.g., help rinse planting media and pests from the plants (e.g., from roots of the plants, etc.), etc.) and to help move (e.g., rinse, etc.) portions of the introduced plant materials through larger sieves until being retained on one of the smaller sieves (depending on sizes of the portions). For example, portions of the plant materials larger than what each of the screens 318, 320, 322, and 324 will allow to pass will be retained on one of the screens 318, 320, 322, and 324; and portions of the plant materials smaller than what respective screens 318, 320, 322, and 324 will retain will pass through the respective screens 318, 320, 322, and 324 to lower ones. The fluid from the second fluid jet 334, and any plant materials smaller than the fourth screen 324, passes through all of the screens 318, 320, 322, and 324 the sieving tower 300 to a waste container (not shown) generally below the sieving tower 300, for example, for disposal, treatment, recycling, etc.

When initial separating operation of the introduced plant is complete, the sieve screens 318, 320, 322, and 324 are moved out of their respective housings 330 (e.g., one at a time, etc.) to remove the separated plant materials retained thereon. In the illustrated embodiment, for example, plant materials retained by the first and second screens 318 and 320 are removed to the waste container (not shown) so as not to interfere with further separating operations (e.g., separating pests from the planting media, etc.). And plant materials retained by the third and fourth screens 322 and 324 are removed and transferred to the elutriation towers 356 and 358 for further separating operation. In other example embodiments, one or more different screens may move in one or more directions different than disclosed herein.

For example, the first screen 318 is moved to the first extended position and rotated (e.g., via its actuator 328, etc.) to remove separated plant materials retained thereon. The first fluid jet 332 operates to spray fluid through the extended screen 318 to help remove the plant materials. The fluid from the first jet 332 and the plant materials removed from the first screen 318 can be collected in the waste container (not shown). The first screen 318 is then moved back to its housing 330. And the second screen 320 is moved to the first extended position and rotated (e.g., via its actuator 328, etc.) to remove separated plant materials retained thereon in similar fashion to that described for the first screen 318.

At about the same time (or before, or after, etc.), the third screen 322 is moved to the second extended position and rotated (e.g., via its actuator 328, etc.) to remove separated plant materials retained thereon. The third fluid jet 336 operates to spray fluid through the extended screen 322 to help remove the plant materials. The fluid from the third jet 336 and the plant materials removed from the third screen 322 are collected in, received in, etc. the transfer unit 340 (e.g., through the funnel 342 of the transfer unit 340, etc.) for subsequent transfer to the first elutriation tower 356 (e.g., via the first discharge 350 of the transfer unit's valve structure 344, etc.).

The third screen 322 is then moved back to its housing 330, and the fourth screen 324 is moved to the second extended position and rotated (e.g., via its actuator 328, etc.) to remove separated plant materials retained thereon. The third fluid jet 336 again operates to spray fluid through the extended screen 324 to help remove the plant materials from the screen 324. The fluid from the third jet 336 and the plant materials removed from the fourth sieve's screen 324 are again collected in, received in, etc. the transfer unit 340 (e.g., through the funnel 342 of the transfer unit 340, etc.), this time for subsequent transfer to the second elutriation tower 358 (e.g., via the second discharge 352 of the valve structure 344, etc.). It should be appreciated that screens can move into and out of housings in any desired order and/or with any desired timing within the scope of the present disclosure.

The fluid from the third jet 336 and the plant materials removed from the third and fourth screens 322 and 324 (and received from the transfer unit 340) pass through respective first and second intermediate sieves inline between the transfer unit 340 and the respective first and second elutriation towers 356 and 358 to separate the fluid from the removed plant material. Fresh fluid is then introduced (e.g., pumped, etc.) through the intermediate sieves to remove the plant materials from the intermediate sieves and transfer them to their respective first and second elutriation towers 356 and 358.

Operation of the elutriation towers 356 and 358 and collection unit 304 to further separate plant materials (e.g., further separation operation, etc. to separate pests from planting media, etc.) and to dispense, deposit, etc. separated plant materials (e.g., pests, etc.) into receptacles will now be described. Operation of the first elutriation tower 356 and first subunit 370 (of the collection unit 304) will be described with it understood that a description of operation of the second elutriation tower 358 and second subunit 372 is substantially the same.

The fresh fluid and separated plant materials from the first intermediate sieve (e.g., from the third screen 322 of the sieving tower 300, etc.) are introduced into a lower portion of the tube 360 of the first elutriation tower 356 and pushed upwardly (e.g., comprising a generally slow fluid flow upwardly, etc.) through the tube 360 by the fresh fluid (e.g., by pressure provided to the fresh fluid via pumps, etc.). Lighter (e.g., finer, less dense, etc.) plant materials (e.g., pests, etc.) pass through (e.g., bubble upwardly through, etc.) the tube 360 (with the upwardly moving fluid), while heavier (e.g., coarser, more dense, etc.) plant materials (e.g., larger planting media materials, etc.) settle from the fluid flow and collect in the tube 360. The lighter plant materials rise with the fluid through the tube 360 because their terminal velocities are lower than the velocity of the rising fluid. The flow rate of the fluid through the tube 360 can be measured (e.g., via the sensors 362, etc.) and adjusted as necessary to promote proper separation of the desired lighter plant materials (e.g., pests, etc.) from the heavier plant materials. For example, as heavier plant materials collect in the tube 360, flow rates through the tube 360 may need to be adjusted to continue proper separation, etc.

The lighter plant materials passing through the tube 360 of the first elutriation tower 356 are transported (e.g., via suitable conduits, etc.) to the first subunit 370 of the collection unit 304 for final separating operation (e.g., separation of pests from other plant materials, planting media materials, etc.). The screens 378 and 380 of the upper and lower sieves 374 and 376 are positioned within their respective housings 384, and the fluid and lighter planting materials from the first elutriation tower 356 are introduced into the subunit 370 (e.g., via suitable conduits and through an upper opening 390 in the first upper sieve's housing, etc.). The fluid and materials selectively move into (and through, depending on their sizes) the screens 378 and 380 of respective sieves 374 and 376 of the subunit 370. The upper screen 378 operates to retain any larger plant materials (e.g., plant materials and larger planting media materials, etc.) passing through the first elutriation tower 356. And the lower screen 380 operates to retain the desired smaller plant materials (e.g., pests, etc.) for subsequent analysis.

When this separating operation is complete, the screens 378 and 380 are moved out of their respective housings 384 to allow removal of the plant materials retained thereon. The upper screen 378 is moved to the first extended position and rotated (e.g., via its actuator 382, etc.) to remove separated plant materials retained thereon to a waste container (not shown), for example, for disposal, treatment, recycling, etc. A fluid jet may operate to spray fluid through the extended screen 378 to help remove the plant materials. The lower screen 380 is moved to the second extended position and rotated (e.g., via its actuator 382, etc.) to remove separated plant materials retained thereon. A fluid jet operates to spray a measured amount of fluid through the extended screen to help remove the plant materials. The fluid from the jet and the plant materials removed from the screen 380 are collected in the receptacle to prepare a sample for subsequent analysis.

The fluid jets are operable to spray any desired, suitable, etc. measured amount of fluid through the extended lower screens 380 of the lower sieves 376 of the subunits 370 and 372 when preparing the sample. For example, the fluid jets of the illustrated embodiment operate to spray 10 milliliters of fluid through the lower screens 380. This fluid, along with the plant materials removed from the screens 380 will comprise at least part of the sample for subsequent analysis. In addition, the fluid sprayed from the fluid jets through the screens 380 can include any suitable fluid for removing plant materials (e.g., pests, etc.) from the screens 380. For example, the fluid may include water, chemical fluids, fluids suitable to stain the plant materials, fluids suitable for enhancing analysis of the removed plant materials, etc. In addition, the fluids can be pressurized and provided from suitable sources (e.g., pressurized containers, etc.) to the collection unit.

Sieving towers may be used with sieves that provide suitable distributions of plant materials for subsequent separation operations (e.g., subsequent elutriation operations, etc.). For example, a narrow size distribution of plant materials received from sieves may be desirable for subsequent separation operations that include elutriation operations. As described above, elutriation generally includes the separation of finer, lighter particles from coarser, heavier particles in a mixture of particles by means of a usually slow upward stream of fluid so that the lighter particles are carried upwardly and the heavier particles settle against the fluid flow. Providing a narrow size distribution of such particles (e.g., of plant materials, etc.) can help control what particles are carried upwardly and what particles settle, and may thus help improve operational efficiency of such elutriation operations. For example, fluid flow through elutriation units can be focused to remove specifically sized desired particles (e.g., pests, etc.). Thus, operation of elutriation units may be set based on the particle distributions from sieves. Moreover, both can be monitored, adjusted, etc. to help improve, optimize, etc. final sample preparation for analysis.

In other example embodiments, processing assemblies may include assemblies to automatically introduce plants into sieve towers, etc. For example, conveyor assemblies, turn table assemblies, picking assemblies, etc. may be used to automatically, continuously, etc. introduce plants for processing (e.g., separation of different plant materials, etc.).

In other example embodiments, processing assemblies may include one or more different and/or one or more additional separating units than disclosed herein. For example, any suitable units operable to separate different plant materials may be used, including, for example, centrifuging units, etc.

In other example embodiments, processing assemblies may include control systems (e.g., internal computer systems, external computer systems, etc.) for use in automating control of at least one or more components the assemblies. The control system may also enable data storage and data manipulation in connection with sample preparation, analysis, etc. Control systems may include, for example, at least one or more of microcontrollers (e.g., including central processing units (CPU), memory, interfaces for communicating with at least one or more components of the assemblies, etc.), user interfaces, etc.

In other example embodiments, processing assemblies may include any combination of one or more components, features, etc. disclosed herein.

FIG. 31 is a block diagram of an example apparatus 400 including one or more aspects of the present disclosure operable for evaluating agricultural products (e.g., plants, etc.), and, for example, samples prepared therefrom, for presence of pests, infestations, pathogen infections, other botanical conditions or characteristics, etc. The illustrated apparatus 400 includes, for example, an example separating unit 402 (e.g., sieving tower 300, elutriation unit 302, collection unit 304, etc.) operable, for example, to separate pests from a plant to produce a sample comprising pests, and an analysis system (e.g., analysis system 10, etc.) operable to analyze the sample (e.g., illuminate at least part of the sample, image the illuminated sample, discriminate pests within the imaged sample, etc.).

In other example embodiments, methods for determining the quantity of pests in samples may generally include one or more of, or any combination of, providing an agricultural sample, illuminating the sample to produce light of mixed wavelengths emitted from at least one discrete spatial sample point of the sample, detecting component wavelengths for each discrete spatial sample point of the sample, processing the detected component wavelengths against a model to determine whether a pest is present in the sample where the model associates the existence of certain component wavelengths with the presence of a pest, calculating the quantity of pests in the sample, dispersing the light emitted from the at least one discrete spatial sample point of the sample into component wavelengths for detection, and producing at least one corresponding spectral image of the sample from the component wavelengths of each sample point, detecting component wavelengths within the corresponding at least one spectral image of the sample, illuminating the sample with a generally thin line of light across a width of at least part of the sample, counting the number of acceptable matches between the detected component wavelengths and the at least one spectral profile, and rinsing the roots and filtering the rinsed material.

In still other example embodiments, methods for quantifying soybean cyst nematode infestation on a soybean plant may generally include one or more of, or any combination of, providing a soybean plant, rinsing roots of the plant to prepare a sample, illuminating the sample to produce light of mixed wavelengths emitted from at least one discrete spatial sample point of the sample, comparing wavelengths of the emitted light to a model to discriminate soybean cyst nematode cysts within the sample, and counting the number of acceptable matches between the wavelengths of the emitted light and the at least one spectral profile.

In further example embodiments, methods for quantifying soybean cyst nematode infestation on soybean plants may generally include one or more of, or any combination of, providing at least one soybean plant having soybean cyst nematodes, removing soybean cyst nematode cysts from the plant to prepare a sample comprising at least soybean cyst nematode cysts, directing a line of light over a portion of the sample to produce emitted light from the sample, dispersing the emitted light to form a spectral image comprising component wavelengths from each of multiple discrete spatial sample points of the sample along the line of light, detecting component wavelengths within the spectral image for each of the discrete spatial sample points along the line of light, repeating the directing, dispersing, detecting processes to scan substantially the whole sample, and producing from the detected component wavelengths at each discrete spatial sample point for each of the scanned portions a hyperspectral datacube for the sample, processing the detected component wavelengths in the hyperspectral datacube against a model to determine whether soybean cyst nematodes are present in the sample. the model associating the existence of certain component wavelengths with the presence of soybean cyst nematodes, and comparing the detected component wavelengths to the model to discriminate soybean cyst nematodes within the sample and counting the number of soybean cyst nematodes within the sample.

In other example embodiments, methods of evaluating soybean cyst nematode resistance in soybean plants may generally include one or more of, or any combination of, introducing soybean cyst nematodes onto a germinated soybean plant, harvesting the soybean plant, separating soybean cyst nematodes from the roots of the soybean plant to prepare a sample comprising soybean cyst nematodes, directing a line of light over a portion of the sample to produce emitted light from the sample, dispersing the emitted light to form a spectral image comprising component wavelength from each of multiple discrete spatial sample points of the sample along the line of light, detecting component wavelengths within the spectral image for each of the discrete spatial sample points along the line of light, repeating the directing, dispersing, and detecting processes to scan substantially the whole sample, producing from the detected component wavelengths at each discrete spatial sample point for each of the scanned portions a hyperspectral datacube for the sample, introducing about 2000 soybean cyst nematode eggs onto the germinated soybean plant, cultivating the germinated plant for about 30 days following introduction of the soybean cyst nematodes, processing the detected component wavelengths in the hyperspectral datacube against a model to determine whether soybean cyst nematodes are present in the sample. the model associating the existence of certain component wavelengths with the presence of soybean cyst nematodes, comparing the detected component wavelengths to the model to discriminate soybean cyst nematodes within the sample and counting the number of soybean cyst nematodes within the sample, scoring the plant based on the number of soybean cyst nematode cysts present in the sample prepared from the plant, and selecting the plant for breeding when scoring is below a predetermined value.

In further example embodiments, assemblies for analyzing samples for one or more predetermined characteristics may generally include one or more of, or any combination of, a carrier for supporting at least one sample, a cuvette configured for reception by the carrier for retaining the sample on the carrier, a light source adjacent the carrier for illuminating at least part of the sample on the carrier, and an imaging device adjacent the carrier for receiving light from the illuminated sample and creating an image of the sample.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method for evaluating plants for presence of pests, the method comprising:

separating pests from a plant to produce a sample of pests for analysis;

illuminating the sample to produce emitted light from the sample;

comparing the emitted light from the sample to a model to discriminate pests within the sample.

2. The method of claim 1, wherein separating pests from the plant includes:

separating planting media and pests from the plant; and separating pests from the planting media.

3. The method of claim 2, wherein separating planting media and pests from the plant includes introducing the plant, planting media, and pests into a sieving unit.

4. The method of claim 2, wherein separating pests from the planting media includes elutriating the planting media and pests that are separated from the plant.

5. The method of claim 4, further comprising depositing the pests separated from the planting media into a receptacle to produce the sample comprising pests for analysis.

6. The method of claim 1, wherein illuminating the sample to produce emitted light from the sample includes illuminating the sample to produce light of mixed wavelengths emitted from at least one discrete spatial sample point of the sample.

7. The method of claim 6, wherein comparing the emitted light from the sample to a model includes comparing wavelengths of the emitted light to a model.

8. The method of claim 1, wherein the model includes at least one spectral profile for the pests.

9. The method of claim 8, further comprising counting the number of acceptable matches between the wavelengths of the emitted light and the at least one spectral profile.

10. The method of claim 1, wherein the pests comprise nematodes, and wherein the plant includes a soybean plant.

11. An assembly for evaluating plants for presence of pests, the assembly comprising:

a separating unit operable to separate pests from a plant to produce a sample comprising pests;

a light source for illuminating at least part of the sample;

an imaging device adjacent the light source for receiving light from the illuminated sample and creating an image of the sample.

12. The assembly of claim 11, wherein the separating unit comprises:

a sieving unit to separate planting media and pests from a plant; and an elutriation tower to separate at least some pests from the planting media.

13. The assembly of claim 12, wherein the sieving unit includes at least two differently sized sieves.

14. The assembly of claim 12, further comprising a transfer unit to receive the planting media and pests from the sieving unit and to transfer the planting media and pests to the elutriation tower.

15. The assembly of claim 12, further comprising a collection unit to receive separated pests from the elutriation tower and to deposit the separated pests into a receptacle.

16. The assembly of claim 15, wherein the collection unit includes at least two differently sized sieves.

17. The assembly of claim 11, further comprising:

a carrier for supporting at least one sample; and a cuvette configured for reception by the carrier for retaining a sample on the carrier.

18. The assembly of claim 17, wherein the carrier includes a calibration block.

19. The assembly of claim 17, wherein the carrier is movable in translation relative to both the light source and imaging device for locating the cuvette in a field of view of the imaging device.

20. The assembly of claim 17, comprising two or more cuvettes each retaining a sample on the carrier.

21. The assembly of claim 11, wherein the light source is configured to emit light having wavelengths between about 450 nanometers and about 900 nanometers.

22. The assembly of claim 11, wherein the imaging device includes a spectrograph and a camera.

23. The assembly of claim 11 wherein operation of the separating unit is automated.

24. A method for quantifying soybean cyst nematode infestation on a soybean plant, the method comprising:
providing at least one soybean plant having soybean cyst nematodes;
separating soybean cyst nematode cysts from the plant to prepare a sample comprising at least soybean cyst nematode cysts;
illuminating the sample to produce light of mixed wavelengths emitted from at least one discrete spatial sample point of the sample;
comparing wavelengths of the emitted light to a model to discriminate soybean cyst nematode cysts within the sample;
calculating the quantity of soybean cyst nematode cysts in the sample.

25. The method of claim 24, wherein separating soybean cyst nematodes cysts from the soybean plant includes:
separating planting media and soybean cyst nematode cysts from the soybean plant; and
separating soybean cyst nematode cysts from the planting media.

26. The method of claim 25, wherein separating planting media and soybean cyst nematode cysts from the soybean plant includes introducing the soybean plant, the planting media, and the soybean cyst nematode cysts into a sieving unit.

27. The method of claim 26, wherein separating planting media and soybean cyst nematode cysts from the soybean plant further includes retaining planting media and soybean cyst nematode cysts in the sieving unit, the method further comprising transferring the retained planting media and soybean cyst nematode cysts to an elutriation tower for separating soybean cyst nematode cysts from the planting media.

28. The method of claim 25, wherein separating soybean cyst nematode cysts from the planting media includes elutriating the planting media and soybean cyst nematode cysts that are separated from the plant.

29. The method of claim 28, further comprising depositing the soybean cyst nematode cysts separated from the planting media into a receptacle to prepare said sample.

30. The method of claim 29, further comprising introducing the separated soybean cyst nematode cysts into a collection unit and retaining the separated soybean cyst nematode cysts on a sieve of the collection unit prior to depositing the soybean cyst nematode cysts into the receptacle.

31. The method of claim 24, further comprising
detecting component wavelengths for each discrete spatial sample point of the sample;
dispersing the light emitted from the at least one discrete spatial sample point of the sample into component wavelengths for detection, and producing at least one corresponding spectral image of the sample from the component wavelengths of each sample point.

32. The method of claim 24, wherein the model includes at least one spectral profile for soybean cyst nematode cysts, the method further comprising comparing the component wavelengths to the at least one spectral profile.

33. The method of claim 24, wherein calculating the quantity of soybean cyst nematode cysts comprises counting the number of acceptable matches between the detected component wavelengths and the at least one spectral profile.

34. The method of claim 24, wherein separating soybean cyst nematode cysts from the plant is automated.

35. A method of evaluating pest resistance in a plant, the method comprising:
harvesting one or more plants comprising pests;
separating the pests from the plant to prepare a sample comprising pests;
illuminating the sample to produce emitted light from the sample;
comparing the emitted light from the sample to a model to discriminate pests within the sample.

36. The method of claim 35, further comprising germinating the one or more plants and introducing pests into the germinated one or more plants prior to harvesting the one or more plants.

37. The method of claim 36, wherein the pests include soybean cyst nematodes.

38. The method of claim 37, wherein the one or more plants include soybean plants.

39. The method of claim 36, wherein the one or more germinated plants are cultivated for about 30 days following introduction of the pests.

40. The method of claim 35, further comprising counting the number of pests within the sample and scoring the one or more plants from which the sample was prepared based on the number of pests present in the sample.

41. The method of claim 40, further comprising selecting the plant for breeding when scoring is below a predetermined value.

* * * * *